US006447485B2

(12) United States Patent
Bierman

(10) Patent No.: US 6,447,485 B2
(45) Date of Patent: Sep. 10, 2002

(54) MEDICAL LINE ANCHORING SYSTEM

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 0 days.

(21) Appl. No.: 09/797,341

(22) Filed: Mar. 1, 2001

Related U.S. Application Data

(62) Division of application No. 08/865,231, filed on May 29, 1997, now Pat. No. 6,213,979.

(51) Int. Cl.[7] ............................................. A61M 5/32
(52) U.S. Cl. .................. 604/174; 604/177; 604/180; 128/DIG. 26
(58) Field of Search ................... 604/174, 175, 604/177, 176, 180, 179; 128/DIG. 26

(56) References Cited

U.S. PATENT DOCUMENTS

| 2,525,398 A | 10/1950 | Collins |
| 2,533,961 A | 12/1950 | Rouseau et al. |
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raffaelli |
| 3,529,597 A | 9/1970 | Fuzak |
| 3,602,227 A | 8/1971 | Andrew |
| 3,630,195 A | 12/1971 | Santomieri |

(List continued on next page.)

FOREIGN PATENT DOCUMENTS

| DE | 2341297 | 4/1975 |
| EP | 0064284 A2 | 4/1982 |
| EP | 0247590 A2 | 12/1987 |
| EP | 356683 A | 7/1989 |
| FR | 1184139 | 7/1959 |
| FR | 2381529 | 9/1978 |
| GB | 2063679 | 6/1981 |
| GB | 2086466 A | 5/1982 |
| WO | WO 80/01458 | 7/1980 |
| WO | WO 85/02774 | 7/1985 |
| WO | WO 91/16939 | 11/1991 |
| WO | WO 92/19309 | 11/1992 |
| WO | WO 96/10435 | 4/1996 |

OTHER PUBLICATIONS

Multiple–Lumen Central Venous Catheerization Product with Arrow+gård™ Antiseptic Surface (Arrow International brochure) (Apr. 1994).
Photographs (4) of Catheter Clamp and Rigid Fastener sold by Arrow International, Inc.

Primary Examiner—Manuel Mendez
(74) Attorney, Agent, or Firm—Knobbe, Martens, Olson & Bear, LLP

(57) ABSTRACT

An anchoring system includes a simply-structured device which permits a portion of a catheter tube or similar medical article to be easily anchored to a patient, desirably without the use of tape or needles and suturing. A unitary retainer desirably includes a base connected to a cover by way of a flexible hinge. The retainer is attached to a flexible anchor pad including an adhesive bottom surface, which can be attached to the patient's skin. A catheter is secured to a fitting, which in turn mounts to the retainer. Mounting the fitting to the retainer can be accomplished by inserting posts of the retainer through holes of the fitting, or by mounting the fitting within a channel defined by mounting structures integral to the retainer. The cover is then positioned over the base, by bending the flexible hinge, and latched to the base. Several embodiments of the latching mechanism are disclosed. In one form, the latching mechanism includes one or more posts on the base which can be releasably locked into corresponding slotted holes in the cover.

22 Claims, 6 Drawing Sheets

U.S. PATENT DOCUMENTS

| | | |
|---|---|---|
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller, et al. |
| 3,900,026 A | 8/1975 | Wagner |
| 3,906,946 A | 9/1975 | Nordstrom |
| 3,942,228 A | 3/1976 | Buckman et al. |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,161,177 A | 7/1979 | Fuchs |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,362,156 A | 12/1982 | Feller, Jr. et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,516,968 A | 5/1985 | Marshall et al. |
| 4,563,177 A | 1/1986 | Kamen |
| 4,633,863 A | 1/1987 | Filips et al. |
| 4,650,473 A | 3/1987 | Bartholomew et al. |
| 4,660,555 A | 4/1987 | Payton |
| 4,711,636 A | 12/1987 | Bierman |
| 4,742,824 A | 5/1988 | Payton et al. |
| 4,808,162 A | 2/1989 | Oliver |
| 4,823,789 A | 4/1989 | Beisang III |
| 4,826,486 A | 5/1989 | Palsrok et al. |
| 4,852,844 A | 8/1989 | Villaveces |
| 4,857,058 A | 8/1989 | Payton |
| 4,863,432 A | 9/1989 | Kvalo |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,955,864 A | 9/1990 | Hajduch |
| 4,976,700 A | 12/1990 | Tollini |
| 4,997,421 A | 3/1991 | Palsrok et al. |
| 5,000,741 A | 3/1991 | Kalt |
| 5,037,397 A | 8/1991 | Kalt et al. |
| 5,073,170 A | 12/1991 | Schneider |
| 5,084,026 A | 1/1992 | Shapiro |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman |
| 5,322,514 A | 6/1994 | Steube et al. |
| 5,330,438 A | 7/1994 | Gollobin et al. |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bieman |
| 5,354,283 A | 10/1994 | Bark et al. |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues, et al. |
| 5,395,344 A | 3/1995 | Beisang, III et al. |
| 5,403,285 A | 4/1995 | Roberts |
| 5,413,562 A | 5/1995 | Swauger |
| 5,443,460 A | 8/1995 | Milusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| D375,355 S | 11/1996 | Bierman |

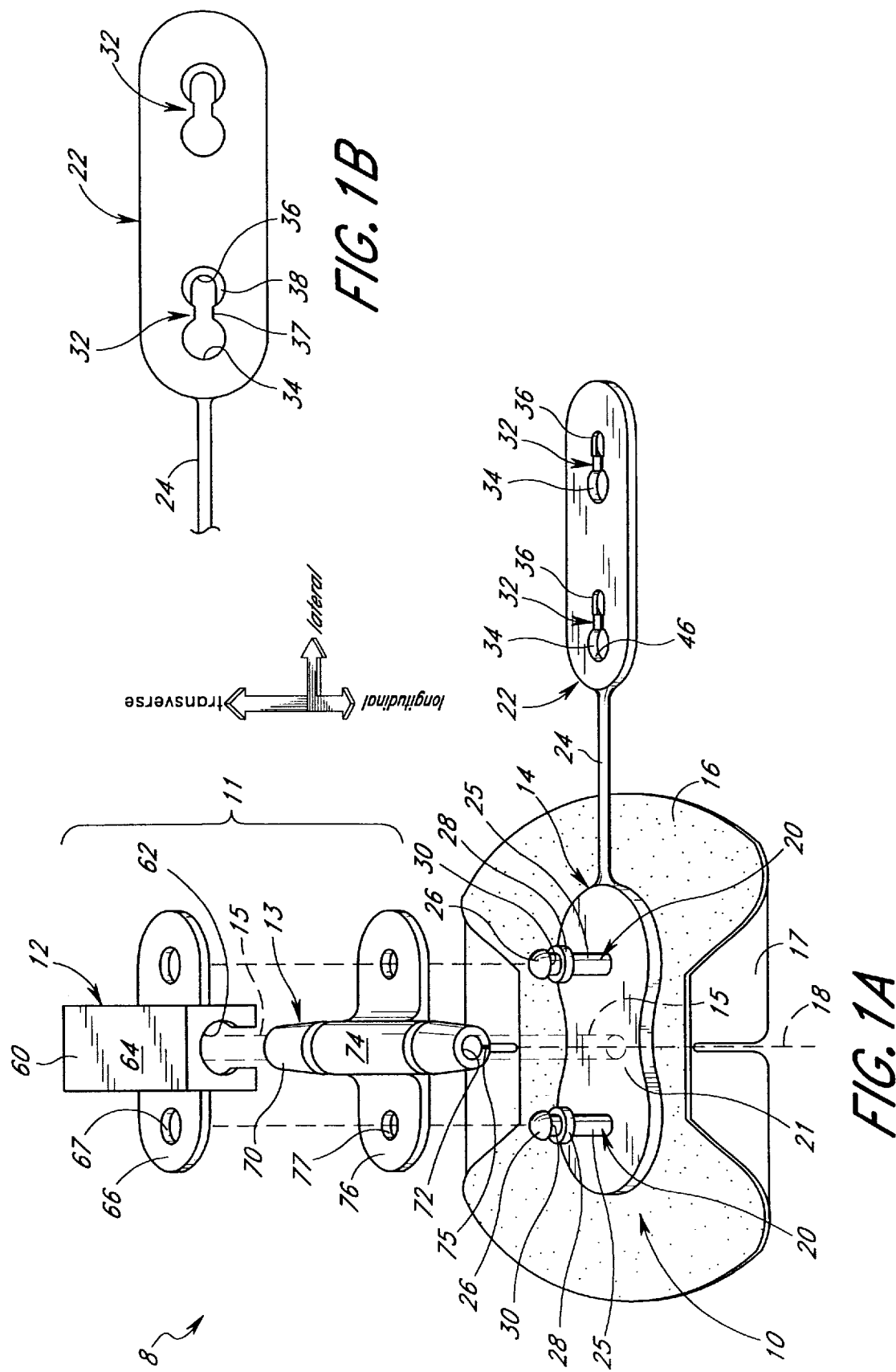

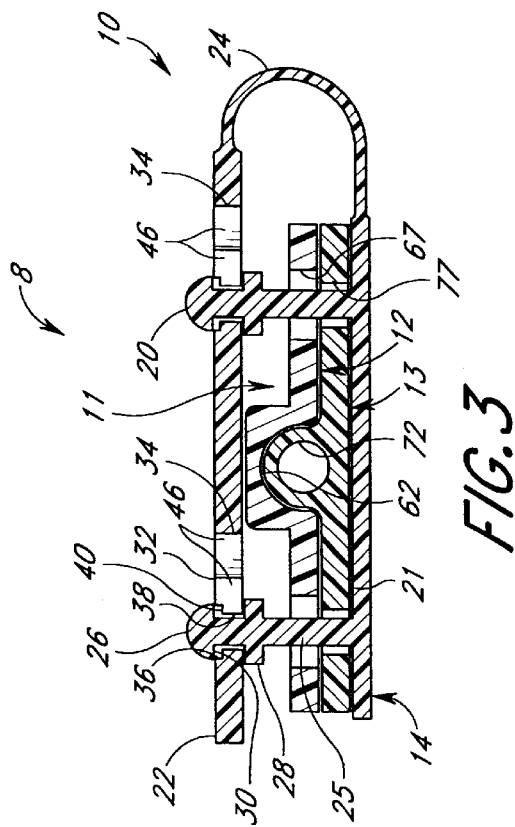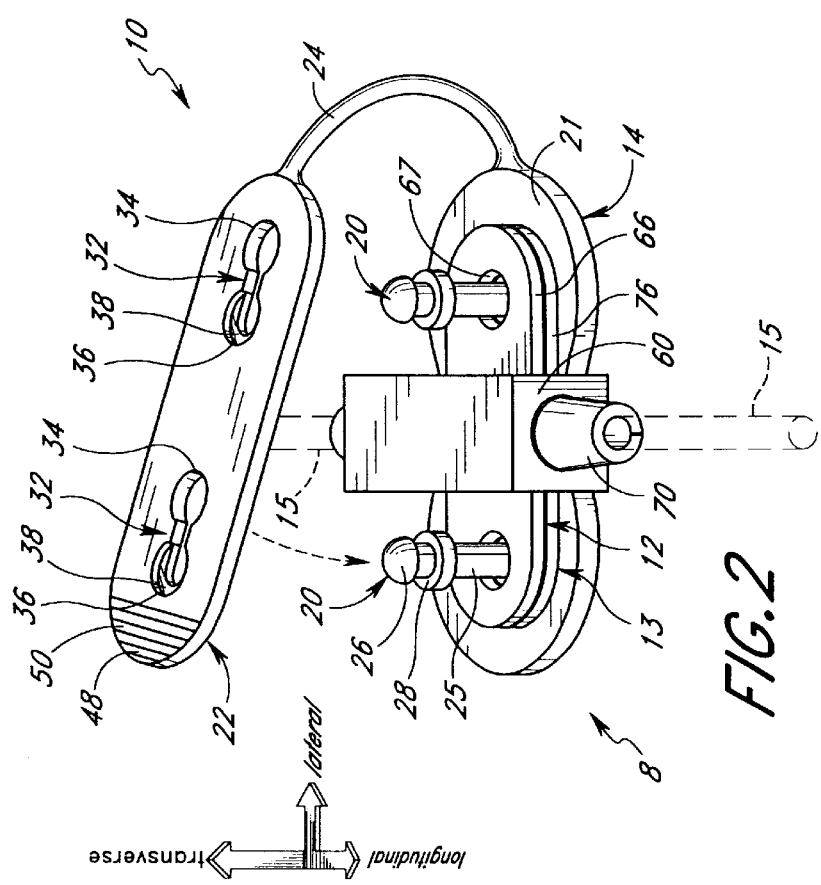

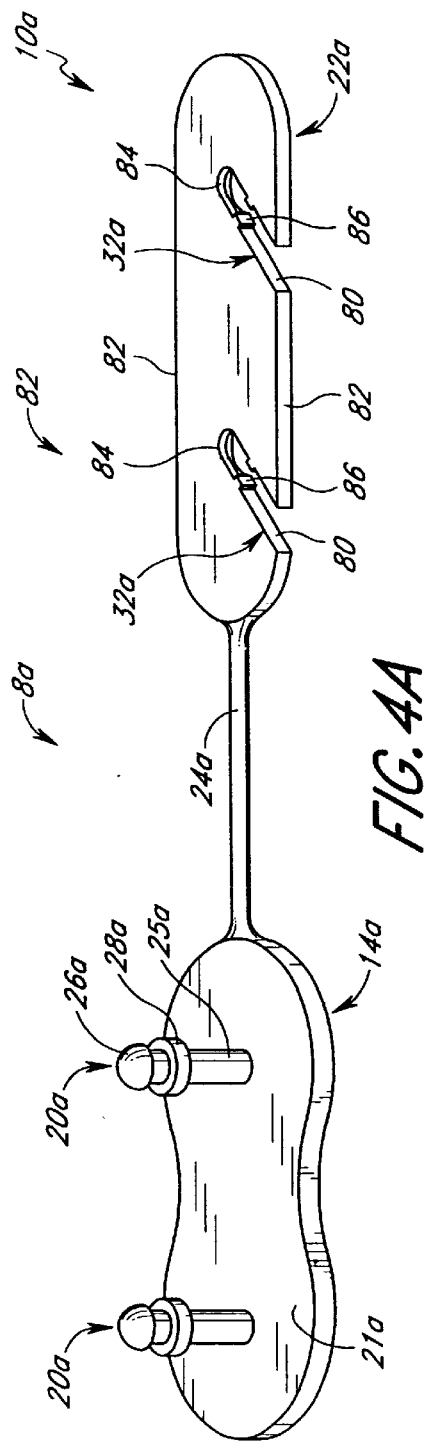
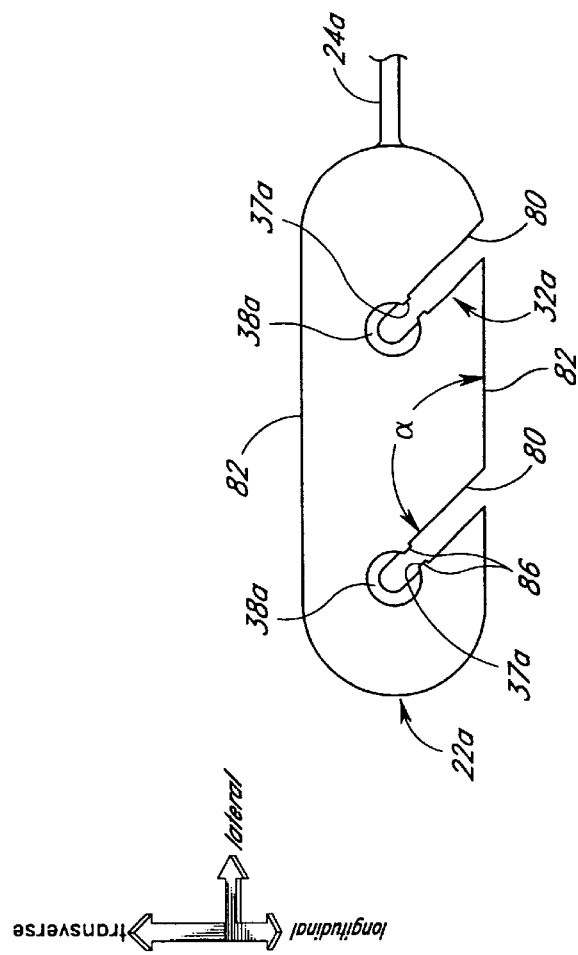
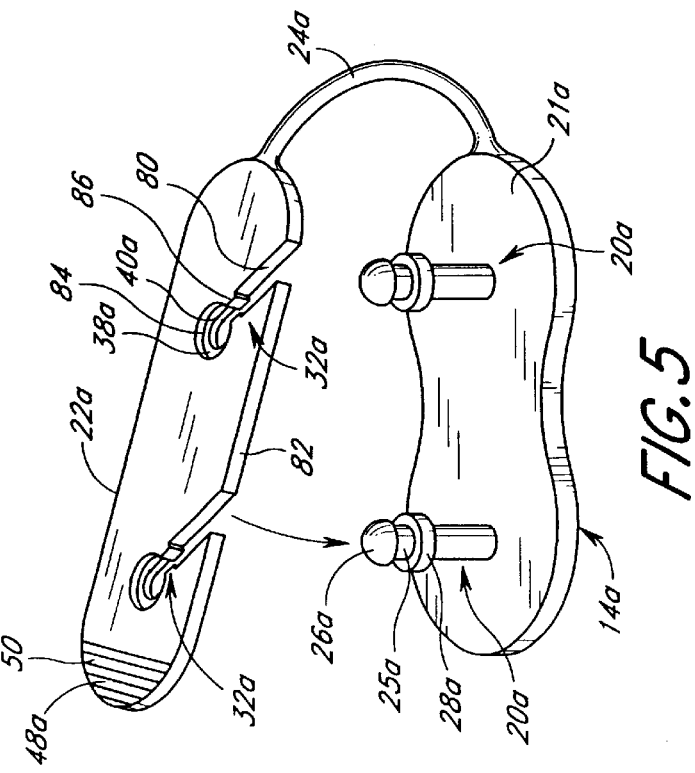

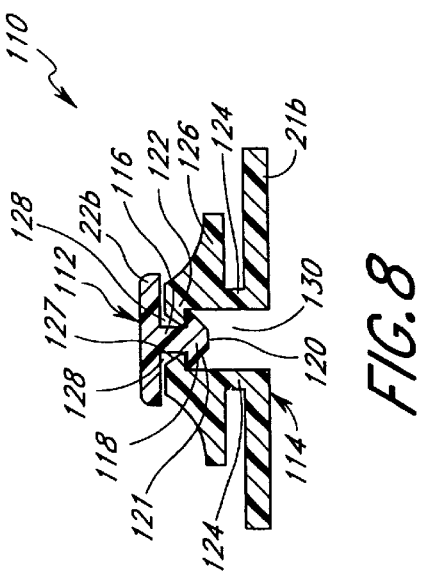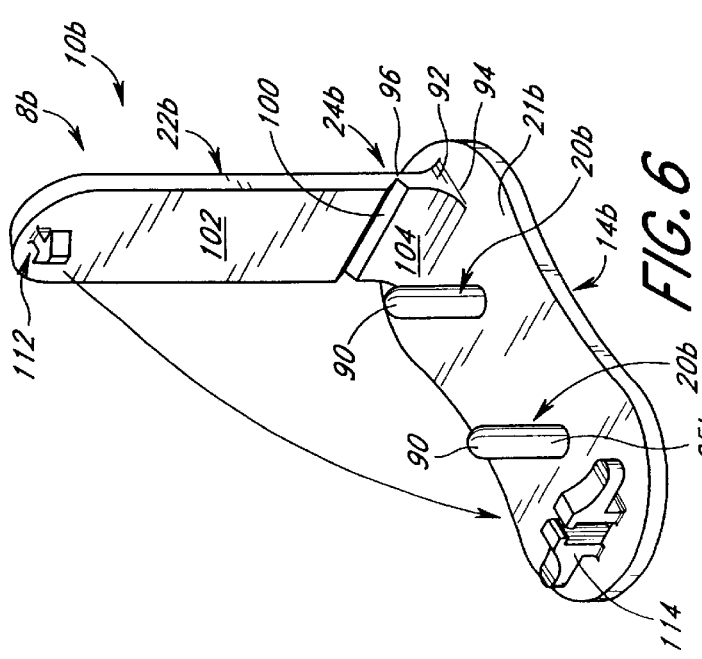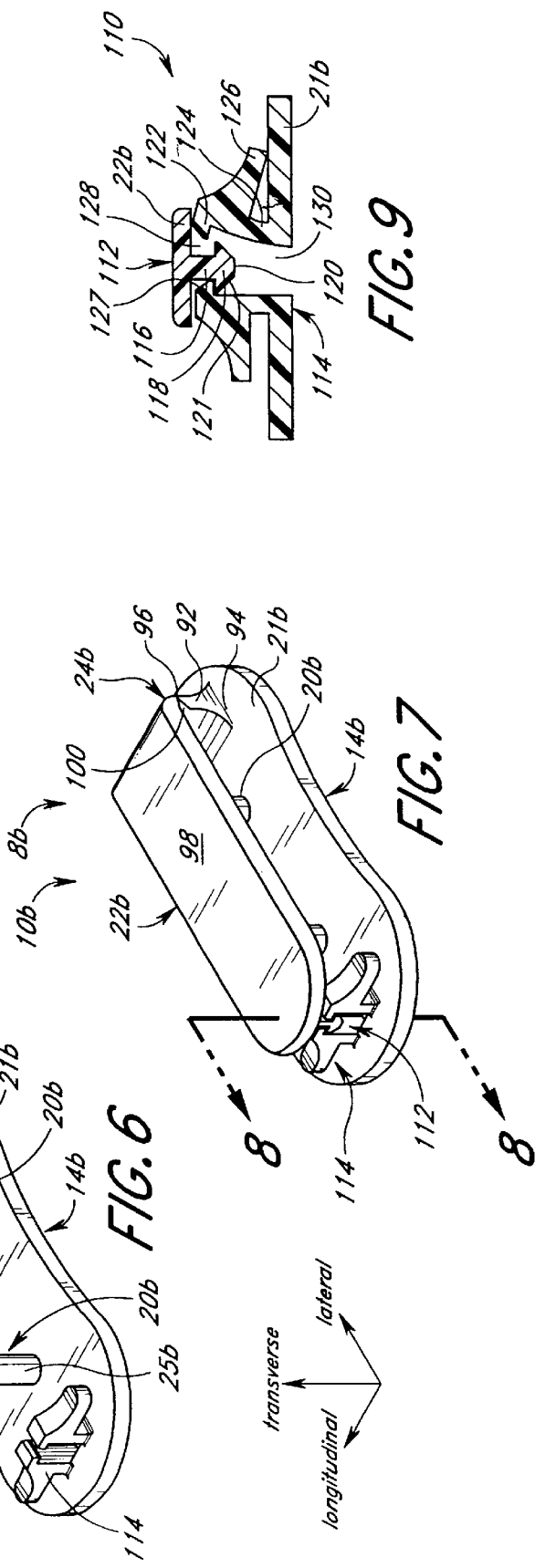

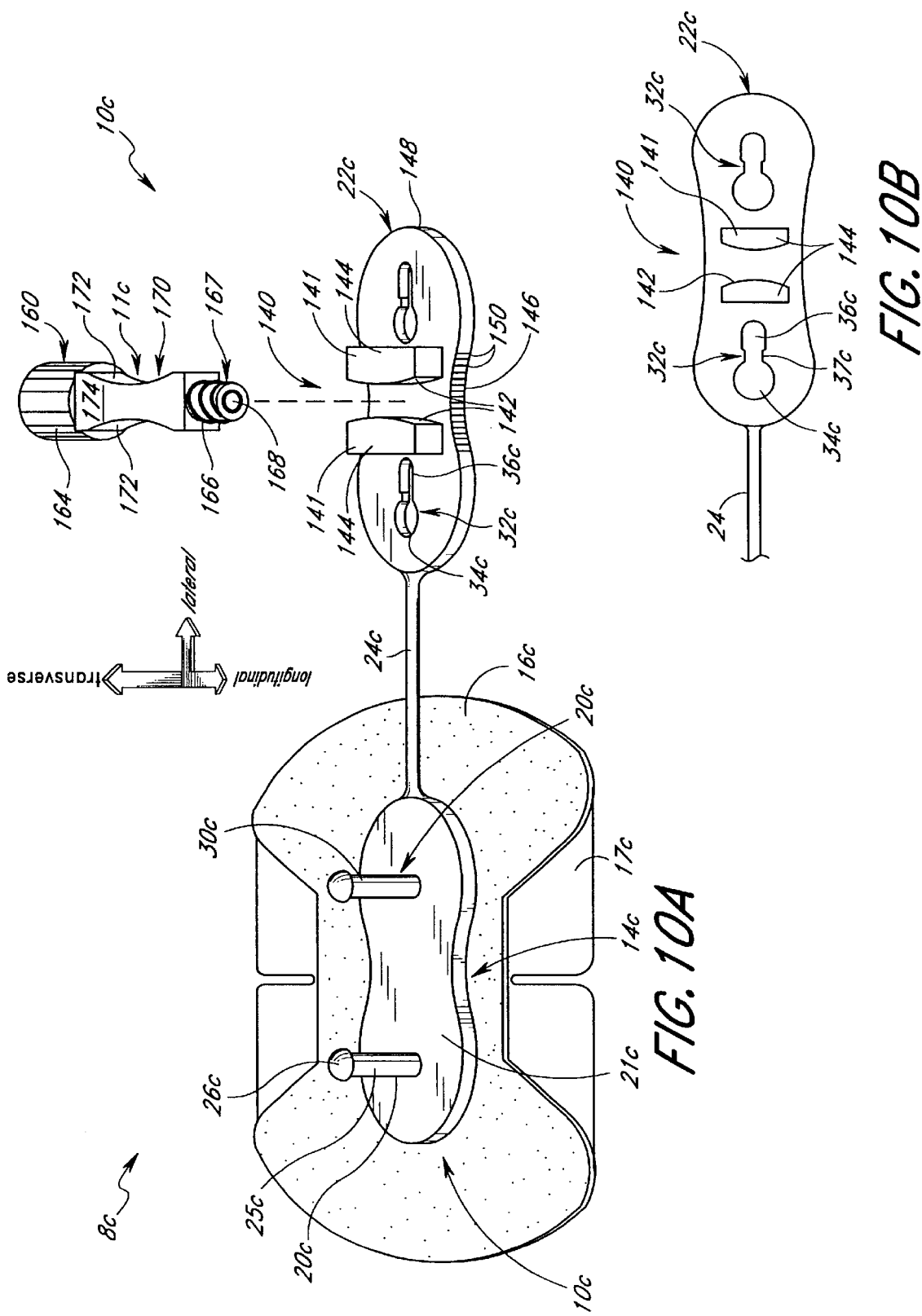

MEDICAL LINE ANCHORING SYSTEM

RELATED CASES

The present application is a divisional of application Ser. No. 08/865,231, filed on May 29, 1997 now U.S. Pat. No. 6,213,979.

BACKGROUND OF THE INVENTION

1. Field of the Invention

The present invention relates to anchoring systems for anchoring medical lines to patients.

2. Description of Related Art

It is very common in the treatment of patients to utilize intravenous (IV) catheters to introduce fluids and medications directly into the bloodstream. In many cases, and particularly with respect to cardiac therapy, the IV catheter is introduced into a central or larger vein located close to the patient's heart. A typical catheter utilized in connection with a central vein is referred to as a "central venous catheter" ("CVC"). A venous catheter peripherally inserted into the central circulation through a vein in the arm is commonly referred to as a "peripherally inserted central catheter" ("PICC").

In these cases, long-term IV infusion typically requires that the catheter remain in place for many days. In order to secure such an IV catheter in position at the insertion site, the catheter often is provided with an integrated or a movable flexible clamp with winged extensions which are sutured to the patient's skin. In other applications, the flexible clamp is covered by a rigid box clamp, which receives the catheter/clamp combination in a friction-fit manner. The rigid box clamp and the flexible clamp have lateral, aligned holes in them, which allow the combination to be sutured to the patient's skin. Although this technique securely attaches the central venous catheter to the patient, it obviously is painful and uncomfortable for the patient. This prior retention procedure is also time consuming and inconvenient, poses the risk of needle-stick to the health care provider, and risks suture-site infection to the patient. In addition, suture material tends to exhibit poor gripping on medical tubes and can cut through the winged extension of the flexible clamp.

SUMMARY OF THE INVENTION

A need therefore exists for a simply-structured anchoring system that affixes a medical line in a fixed position, but releases the medical line for dressing changes or other servicing.

On aspect of the present invention thus involves an anchoring system for securing a medical line to the body of a patient. The system comprises a retainer including a base that defines a receiving area for receiving a portion of the medical line. A cover is permanently coupled to the base. The cover is movable between a closed position, in which at least a portion of the cover extends over at least a portion of the receiving area, and an open position, in which the receiving area is at least partially open. A latching mechanism operates between the base and the cover to releasably latch the cover to the base with the cover in the closed position. Interacting structure is located generally beneath the cover with the cover in the closed position. The interacting structure is adapted to limit movement of the medical line through to the retainer when the catheter is placed within the receiving area.

Another aspect of the present invention involves an anchoring system for securing a medical line to the body of a patient. The system includes a fitting adapted to engage with the medical line and having at least one opening. A retainer comprises a base including a platform and at least one post extending from the platform and arranged to interact with the hole of the fitting. A cover is movably coupled to the base so as to be moved between an open position and a closed position. A latching mechanism operates between the cover and the base to releasably latch the cover to the base in the closed position.

In accordance with an additional aspect of the present invention, an anchoring system for securing a medical line to the body of a patient is provided. The anchoring system comprises an adaptor having an adaptor body with a longitudinal axis defined between first and second ends. A first connector is located at the first end of the adaptor for connection to a first medical line, and a second connector is located at the second end for connection to a second medical line. A retainer includes a base and a cover permanently coupled to the base. The cover is movable between an open position and a closed position. A latching mechanism releasably latches the cover to the base in the closed position. And a channel is arranged to lie between the base and the cover in the closed position. The channel is shaped to retain the adaptor between the cover and the base with the cover in the closed position to inhibit movement of the adapter in a direction generally parallel to the adapter's longitudinal axis. An adhesive layer is attached to the retainer and is adapted to adhesively secure the retainer to the body of a patient.

A preferred method of anchoring a medical line to a patient involves providing a retainer including a base having a plurality of posts, and a cover attached to the base by a flexible leash. The provided cover also includes a corresponding plurality of openings with each opening comprising a slot. The retainer is coupled to an adhesive layer. The anchoring system is positioned on the body of the patient, and the adhesive layer is attached to the body of the patient. A medical device is arranged between the posts of the base. The cover is positioned over the base to bring the openings of the cover in proximity with the posts of the base. The cover is shifted relative to the base to engage the posts with the slots of the openings.

Further aspects, features, and advantages of the present invention will become apparent from the detailed description of the preferred embodiments that follow.

BRIEF DESCRIPTION OF THE DRAWINGS

The above-mentioned and other features of the invention will now be described with reference to the drawings of several preferred embodiments of the present anchoring system. The illustrated embodiments of the anchoring system are intended to illustrate, but not to limit the invention. The drawings contain the following figures:

FIG. 1A is a perspective view of an anchoring system in accordance with a preferred embodiment of the present invention and illustrates a retainer of the anchoring system in an open position together with an exemplary catheter wing clamp fitting (the components of which are illustrated as exploded above the retainer);

FIG. 1B is a bottom plan view of a cover of the retainer of FIG. 1A;

FIG. 2 is a perspective view of the anchoring system of FIG. 1A with the cover of the retainer shown in a partially closed position;

FIG. 3 is a cross-sectional view of the anchoring system of FIG. 2, with the retainer shown in a completely closed position and the catheter wing clamp fitting assembled and anchored therein;

FIG. 4A is a perspective view of a retainer in accordance with another preferred embodiment of the present invention, shown in an open position;

FIG. 4B is a bottom plan view of a cover portion of the retainer of FIG. 4A;

FIG. 5 is a perspective view of the retainer of FIG. 4A, shown in a partially closed position;

FIG. 6 is a perspective view of a retainer in accordance with another preferred embodiment of the present invention, shown in an open position;

FIG. 7 is a perspective view of the retainer of FIG. 6, shown in a closed position;

FIG. 8 is a cross-sectional view of the retainer of FIG. 7, taken along the line 8—8;

FIG. 9 is a cross-sectional view of the retainer according to FIG. 8, but with a tang shown in a release position;

FIG. 10A is a prospective view of an anchoring system in accordance with an additional preferred embodiment of the present invention and illustrates a retainer of the anchoring system in an open position and together with an exemplary catheter adaptor;

FIG. 10B is a bottom plan view of a cover portion of the retainer of FIG. 10A;

DETAILED DESCRIPTION OF THE PREFERRED EMBODIMENTS

Figure 12:
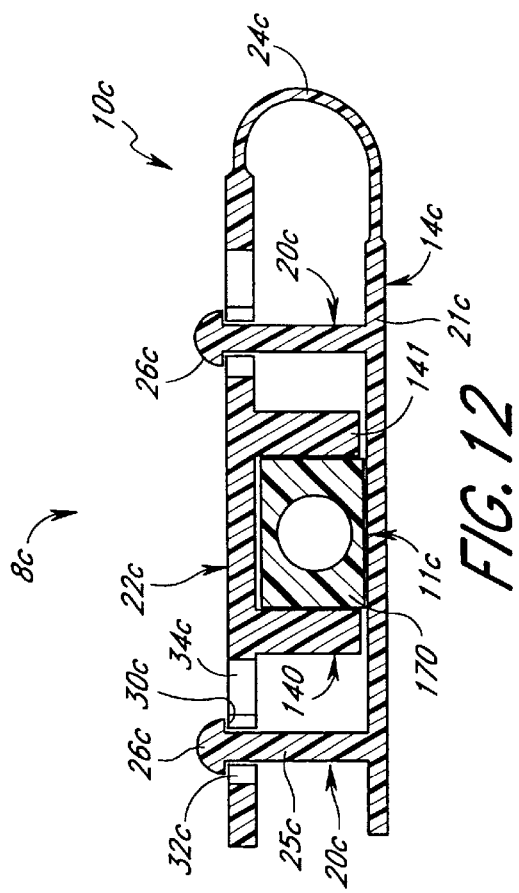
FIG. 12 is a cross-sectional view of the retainer according to FIG. 11, shown in a completely closed position, with the catheter adaptor anchored therein.

The present embodiments of the medical line anchoring system are disclosed in the context of an exemplary central line catheter. The principles of the present invention, however, are not limited to PICCs or CVCs. Instead, it will be understood by one of skill in this art, in light of the present disclosure, that the anchoring systems and retainers disclosed herein also can be successfully utilized in connection with other types of medical lines, including tubes for fluid communication and electrical wires. For example, but without limitation, the retainers disclosed herein can retain CVCs, PICCs, Foley catheters, and hemodialysis catheters, surgical drainage tubes, feeding tubes, chest tubes, nasogastric tubes, scopes, as well as with electrical wires or cables connected to external or implanted electronic devices or sensors. One skilled in the art may also find additional applications for the devices and systems disclosed herein. Thus, the illustration and description of the anchoring system 8 in connection with a catheter is mainly exemplary of one possible application of the system.

Each of the embodiments described herein employ the same basic concepts characteristic of the improved anchoring system, namely releasable attachment of a medical line to a patient. The anchoring systems also all include interacting structure that operates between a retainer of the anchoring system and a fitting which in some applications is releasably attached to the medical line and in other applications is integrally formed with the medical line. The interacting structure between the retainer and the fitting generally inhibits relative movement between the medical line and the anchoring system in at least one degree of freedom.

To assist in the description of the components of the anchoring systems and retainers disclosed herein, the following coordinate terms are used. A longitudinal axis is generally parallel to a section of the medical line to be retained by the anchoring system, generally in the plane of a retainer base (discussed below). A lateral axis is generally perpendicular to the longitudinal axis within the plane of the base. A transverse axis extends transverse to both the longitudinal and lateral axes. A number of the figures illustrate this coordinate system to the side of the anchoring system. In addition, as used herein, the "longitudinal direction" refers to a direction substantially parallel to the longitudinal axis. "The lateral direction" refers to a direction substantially parallel to the lateral axis. And, "the transverse direction" refer to a direction substantially parallel to the transverse axis. These coordinates are used to describe structures and movement of the anchoring system of each embodiment. A detailed description of each embodiment, and its associated method of use, now follows.

FIGS. 1 to 3 illustrate an anchoring system 8 constructed in accordance with a preferred embodiment of the present invention. The system 8 includes a retainer 10 which is configured to retain a catheter, either directly or by way of a fitting 11. In the illustrated embodiment, the fitting 11 comprises a catheter box clamp 12 and a soft wing clamp 13 for use with a central line catheter 15.

The retainer 10 includes a base 14. The base 14 of the retainer 10 is attached to an anchor pad 16, which forms a part of the anchoring system 8. The base 14 desirably is secured to the anchor pad 16 by a solvent bond adhesive, such as cyanoacrylate or other bonding material. One such adhesive is available commercially as Part No. 4693 from the Minnesota Mining and Manufacturing Company (3M).

The anchor pad 16 comprises a flexible structural layer for securing the retainer 10 to a patient's skin. The pad desirably comprises a laminate structure with an upper cellulose foam layer (e.g., closed-cell polyethylene foam), and a bottom adhesive layer. The adhesive desirably is a medical-grade adhesive and can be either diaphoretic or nondiaphoretic, depending upon the particular application. Such foam with an adhesive layer is available commercially from New Dimensions in Medicine of Columbus, Ohio. Although not illustrated, it will be understood that the retainer and/or anchor pad can include suture holes in addition to the adhesive layer to further secure the anchor pad to the patient's skin.

An upper surface of the foam layer is roughened by corona-treating the foam with a low electric charge. The roughened or porous upper surface of the anchor pad 16 improves the quality of the adhesive joint formed by the cyanoacrylate (or by another type of adhesive or bonding material) between the base 14 to the anchor pad 16. In the alternative, the flexible anchor pad 16 can comprise a medical-grade adhesive bottom layer, an inner cellulose foam layer and an upper paper or other woven or non-woven cloth layer.

A removable paper or plastic backing 17 desirably covers the bottom adhesive surface before use. The backing 17 preferably resists tearing and is divided into a plurality of pieces to ease attachment of the pad to a patient's skin. Desirably, the backing 17 is split along a center line 18 of the flexible anchor pad 16 in order to expose only half of the adhesive bottom surface at one time. The backing 17 also advantageously extends beyond at least one edge of the anchor pad 16, as illustrated, to facilitate removal of the backing 17 from the adhesive layer.

In the illustrated embodiment, the anchor pad 16 also desirably includes a pair of opposing concave sections that narrows the center of the anchor pad proximate to the base 14. As a result, the peripheral ends of the anchor pad 16 have more contact area to provide greater stability and adhesion to a patient's skin, while allowing the retainer 10, which is located at center section of the anchor pad 16, to be placed adjacent to an insertion site of the catheter 15.

Although the anchor pad 16 has not been shown in the other drawings that illustrates this embodiment, nor in some of the drawings illustrating the other embodiments, it will be understood that a similar flexible anchor pad is included to secure the retainer to the patent's skin with each embodiment.

The base 14 and the catheter 15 desirably include interacting structure to couple the catheter 15 to the base 14. As will be clear from the disclosure below, the interacting structure mounts the medical line either directly or by way of a fitting (e.g., the box clamp 12 and soft wing clamp 13) to the base 14. In the latter case, a portion of the interacting structure desirable is formed on the fitting and another portion of the interacting structure is formed on the retainer. The term "mount," when used with reference to the relation between the catheter or fitting and the retainer, does not necessarily imply that the catheter 15 or fitting 11 are immobilized or fixed. Rather, this term is meant to describe the condition in which the interacting structure inhibits movement of the catheter 15 relative to the retainer 10 in at least one degree of freedom (e.g., rotational, lateral, longitudinal or transverse). In the illustrated embodiment, as well as in those later described, the interacting structure inhibits movement of the catheter 15 at least in the longitudinal direction.

In the illustrated embodiment, a portion of the interacting structure on the base 14 comprises at least one post 20 which extends upwardly from a relatively rigid platform 21. The base 14 desirably includes a pair of posts 20. The base can also include additional posts to suit a specific application. For example, where the retainer is designed to secure a relatively large fitting, the base can include four posts arranged at the corners of a rectangle, for greater stability. And, three posts can be used to firmly anchor a Y-site fitting.

Each post 20 includes a shank or shaft 25, attached to and extending upwardly from the platform 21. The posts 20 can have a variety of lengths and a variety of distances between them, depending upon the particular application and the particular fitting 11 with which they are to interact to mount the catheter 11. For anchoring catheters and medical tubing, each post 20 desirably has a length of about 4 mm to 20 mm, and more particularly a length of about 6 mm; however, longer or shorter lengths also are possible. The posts 20 are laterally spaced at least wide enough to accommodate the medical line to be anchored, and in the illustrated embodiments, the posts 20 are spaced to accommodate the fitting 11 which secures the medical line. Desirably, the posts 20 are spaced apart by a distance between 5 mm and 40 mm, and more particularly by a distance equal to about 15 mm. The shaft 25 of each post 20 has a diameter sufficient to perform its structural function, as described in more detail below, and depends upon the material chosen for the base 14 and shafts 25. The illustrated posts 20 comprise a polymer plastic material, with a diameter between 0.5 mm and 3 mm and particularly about 1.7 mm.

At least one protrusion extends radially from the shaft. In the illustrated embodiment, the protrusion comprises an enlarged tip or head 26 at the end distal from the platform 21. As seen in FIG. 1, at least a portion of the head 26 of each post 20 is larger than the diameter of the shaft 25, desirably having a maximum diameter of 1.1 to 1.5 times the diameter of the shaft 25. In the illustrated embodiment, the head 26 has a generally hemispherical shape with a smooth surface and a maximum diameter at an overhanging lower surface or underside 30. It will be understood, however, that the head 26 can take a variety of other shapes, such as for example, solid or hollow conicals, arrowheads, barbs, spheres, mushroom heads, and other types of radially projecting structures. A relatively blunt end of the head 26 is preferred to avoid snagging on materials such as a health care provider's latex gloves or sheets on the patient's bed.

A cover 22 is flexibly coupled to the base 14 by way of a flexible coupling. In the illustrated embodiment, the coupling comprises a flexible leash 24. The leash 24 can take any number of forms to mechanically connect the base 14 to the cover 22 while permitting movement of the cover 22 relative to the base 14 so as to enable engagement or disengagement of these parts, as described below. In the illustrated embodiment, the leash 24 comprises a band of flexible material. The leash 24 desirably is integrally molded with the base 14 and the cover 22. The illustrated leash 24 has a longitudinal width of about 0.5 mm to 5 mm, desirably about 1 mm, and a similar depth or transverse dimension. The length of the leash 24 depends in part upon the height of the post 20. Desirably, the leash 24 is longer than the height of the post 20, to allow some leeway in engaging or disengaging the base 14 with the cover 22, as will be understood by one of skill in the art in light of the disclosure herein. While the leash 24 desirably is generally oblong in cross-section, as illustrated, and fixes an orientation of the cover 22 relative to the base 14, it will be understood that the leash can also have a string-like (e.g., rounded) configuration and allow rotation about the lateral axis.

The cover 22 comprises an elongate member which can be formed of the same polymer or plastic material as the base 14, and desirably is integrally molded with the base 14. The cover 22 desirably has a shape that is generally coextensive with the platform 21 of the base 14. The cover 22 can be smaller; however, the cover should have a length in the lateral direction at least large enough to extend over the space between the posts 20 and a width in the longitudinal direction that is wider than the posts 20. The width of the cover 22 desirably is sufficient to stabilize a section of the catheter 15 within the retainer 10. In particular, the width of the cover 22 preferably generally matches the longitudinal length of the fitting 11. The corners of the cover are also desirably rounded to avoid snagging on materials such as the latex gloves worn by the health care provider, bed sheets, etc. In the illustrated embodiment, the cover 22 generally has an elliptical shape for this purpose.

As shown in FIG. 2, the illustrated cover 22 also desirably includes a textured portion 48, such as that formed by longitudinal ridges 50 in the cover surface at an end of cover 22 opposite of the leach 24. It will be understood that any well known form of texturing such as, for example, a roughened surface can be used in place of ridges. The textured portion 48 improves the health care provider's grip on the cover 22.

The base 14 and cover 22 are further releasably connected by a latching mechanism. The latching mechanism permits the cover 22 to be engage with the base 14 in a closed position, as illustrated in FIG. 3. The cover 22 also can be disengaged from the base 14 and moved to an open position, as shown in FIG. 1A.

The latching mechanism includes interengaging structures formed on the base 14 and on the cover 22. In the illustrated embodiment, the portion of the latching mechanism on the base 14 is formed by at least one of the posts 20 with it enlarged head 26. Desirably, the latching mechanism involves the posts 20 that lie on opposite sides of the catheter 15 when the catheter 15 is properly positioned on the retainer 10.

A cover portion of the latching mechanism includes at least one opening 32 formed in the cover 22, and desirably includes the same number of openings 32 as there are posts 20 on the base 14. The illustrated cover 22 thus includes two openings 32 with corresponding points of the openings 32 being spaced by approximately the same distance as the two posts 20 on the base 14, desirably by between about 5 mm and 40 mm, and particularly about 15 mm. Each opening 32 is arranged in the cover 22 to cooperate with the corresponding post 20. It will be understood that, in other arrangements of the latching mechanism are possible where the posts are on the cover, the openings are formed in the base, as described in more detail below.

Each opening 32 shown in FIGS. 1–3 is defined by a central hole 34 with at least one slot 36 extending to one side, desirably laterally adjacent to and intersecting with the central hole 34 at a narrow waist opening 37. The central hole 34 is sized and shaped to accommodate the largest diameter of the post head 26. The illustrated slot 36 extends in the lateral direction from the central hole 34 with the lateral axis of the slot 36 being substantially collinear with a center line of the cover 22 extending in the lateral direction. It will be understood that the slots 36 on the cover 22 can extend from the central hole 34 in any direction, though both slots 36 desirably extend in the same general direction. In other arrangements, more than one slot can extend from each central hole.

The width of the illustrated slot 36 in the longitudinal direction is smaller than the central hole 34 and is smaller than the largest diameter of the head 26. The slot width desirably ranges from slightly smaller to slightly larger than the diameter of the shaft 25.

The interengagement between the posts 20 and the openings 32 on the cover 22 thus form the latching mechanism that releasably secures the cover 22 to the base 14. When the post shaft 25 is positioned in the slot 36, the cover 22 can not be lifted from the retainer base 14 in the transverse direction, as described in more detail below.

As best seen from the plan view of FIG. 1B, the cover 22 desirably includes a post retention mechanism to inhibit unintentional retraction of a post 20 from the slot 36. In the embodiment of FIGS. 2–3, the retention mechanism includes a lip 38 of cover material that forms a depression 40 (FIG. 3). The depression 40 is sized slightly smaller than the lower surface 30 of the post head 26. The retention mechanism of the illustrated slotted hole 36 further comprises the waist opening 37 (FIG. 18), which has a slightly smaller diameter than the shaft 25. The longitudinal dimension of the slot 36 widens to slightly larger than the diameter of the shaft 25 between the lip 38 of the cover 22. While not illustrated, the retention mechanism can also be formed by arranging the slots at a slight deviation from parallel to one another to increase the friction between the cover 22 and the posts 20.

The retainer 10 also desirably includes a locator device to locate the cover 22 at a desired distance from the platform 21. In the illustrated embodiment, each post 20 includes an annular ring 28 positioned between the platform 21 and the head 26 for this purpose; however, other types of protuberances (e.g., small bumps or ribs) can also serve this purpose.

The annular ring 28 is spaced below the head 26 along the shaft 25 by a distance sufficient to accommodate the thickness of the cover 22 when latched together. The ring 28 desirably is located between about1 mm and 4 mm below the lower surface 30 of the head 26. Like the head 26, the annual ring 28 is larger in diameter than the shaft 25, desirably 1.1 to 2.0 times the diameter of the shaft 25. Most desirably, the ring 28 is slightly larger than the maximum diameter of the head 26.

As mentioned above, the base 22, leash 24 and cover 22 desirably are integrally formed to make a unitary retainer 10. This can be accomplished in any of a variety of ways well known to one of skill in the art. For instance, the entire retainer can be injection molded, in order to reduce fabrication costs. Additionally, features such as the leash 24 are desirably flexible. Suitable plastics which account for these considerations include polypropylene, polyethylene, and the like. Desirably, the illustrated retainer 10 comprises injection molded polyethylene or polypropylene.

The anchoring system 8 can also include the fitting 11 for mounting a medical line (e.g., catheter) to the retainer 10. In the exemplary application illustrated in FIGS. 1–3, the fitting 11 takes the form of the box clamp 12 and the soft wing clamp 13. Mounting of the fitting 11 (or catheter directly) to the retainer 10 is achieved by way of the interacting structures, a portion of which comprises surfaces or structures of the retainer 10 and another portion of which comprises surfaces or structures of the fitting 11 (or catheter, if directly coupled).

The box clamp 12, best seen from the view of FIG. 1, is a relatively small, rigid wing-shaped device having a configuration similar to that of conventional box clamps in common usage today in suturing attachment systems. The box clamp 12 includes a central elongate body 60 having a longitudinal groove 62 formed on the underside and a box-shaped upper surface 64. The longitudinal groove 62 is generally U-shaped and is sized to receive the body of a catheter and/or associated fluid line, and more desirably is sized to receive the wing clamp 13. At least one end, and preferably at both ends of the longitudinal groove 62, the body 60 of the box clamp 12 narrows the opening of the longitudinal groove 62. That is, the longitudinal groove 62 at either end extends through an arc which is greater than 180E about an axis of the longitudinal groove 62. The groove also can have a uniform cross section along its length so that the wall of the entire groove extends through an arc greater than 180E. The box clamp 12 desirably is formed of a relatively rigid material, such as polycarbonate.

A pair of lateral wings 66 extend roughly perpendicularly from the body 60 of the box clamp 12, each including a hole 67 therethrough. Each hole 67 is sized and shaped to receive the head 26 and the collar 28 of one of the posts 20.

The soft wing clamp 13 has a configuration similar to that of the box clamp 14, including a central elongate body 70 defining an inner cavity 72 and an outer surface 74. The inner cavity 72 is sized to surround a portion of a catheter. The wing clamp 13 is constructed from a soft, pliable or flexible material such as, for example, latex or the like. The central elongate body 70 includes a longitudinal slit 75 along its underside. The slit 75 can be expanded due to the pliable nature of the wing clamp 13. Thus, the wing clamp 13 is capable of being placed on and surrounding and longitudinally contacting in a frictional manner a portion of the catheter. This frictional contact between the soft wing claim 13 and the catheter generally prevents relative movement between these articles.

Lateral wings 76 extend roughly perpendicularly from the body 70 of the soft wing clamp 13, each including a through-hole 77. Each hole 77 is sized and shaped to receive the head 26 of one of the posts 20. As the material surrounding the wing hole 67 is pliable in the illustrated embodiment, the hole 67 can be smaller than the corresponding box clamp hole 67 and even smaller than the post head 26, yet still be stretched to receive the post head 26; the through-hole 77, however, desirably is larger than the post head 26 and generally equal in size to the corresponding hole 67 in the box clamp 12.

The illustrated box clamp 12 and soft wing clamp 13 are commercially available from Arrow® for use with its CVC. Other clamps with suture wing extensions are currently in commercial use with Quinton® Hemodialysis catheters, Cook® PICC's, Baxter® CVCs and B. Braun CVCs. The skilled artisan will find application for the present invention with any of these and many other clamp configurations. As will be clear from a discussion of the embodiment of FIGS. 10–12, the fitting 11 (box clamp/soft wing clamp combination) can also be replaced with an inter-line connector or adaptor, such as those used to connect the catheter to a supply, delivery or drainage line.

FIG. 3 illustrates the interengagement of the components of the anchoring system 8, in accordance with the present embodiment. The box clamp 12 and soft wing claim 13 are shown engaged with the posts 20 and retained between the base 14 and cover 22 of the retainer 10.

As noted, the groove 62 of the box clamp 12 is configured to receive the soft wing clamp 13. In particular, the groove 62 is sized and shaped to receive the outer surface 74 of the elongate body 74 on the soft wing clamp 13. The wings 66 of the box clamp 12 have approximately the same size and shape as the wings 76 of the soft wing clamp 13. When the wings 66, 76 are aligned, the box clamp holes 67 are correspondingly aligned with the soft wing clamp holes 77.

Together, the box clamp 12 and the soft wing clamp 13 form the fitting 11 for mounting in the retainer 10. In the illustrated embodiment, the retainer 10 has been sized for retention of the conventional box clamp 12 and soft wing clamp 13. Accordingly, the holes 67, 77 of the fitting 11 are spaced by approximately the same distance as the posts 20 on the retainer base 14. The box-like upper surface 64 of the box clamp 12 is sized and shaped to fit between the posts 20. Accordingly, a lateral dimension of the elongate body 60 is smaller than the spacing between the posts 20 (i.e., the elongate body 60 is located between and spaced from holes 67 on the box clamp wings 66), while the height of the fitting 11 (formed by the height of the box clamp 12 plus the thickness of the soft wing clamp wings 76) is smaller than the height of the posts. Desirably, the height of the fitting is smaller than the height of the shaft 25 up to the underside 30 of the post head.

The interaction between the posts 20 and the openings 67, 77 of the fitting 11 mount the fitting 11 on the base 14. Accordingly, this interacting structure between the retainer 10 and the fitting 11 inhibits movement of the catheter 15 relative to the retainer 11 in at least the longitudinal and lateral directions. It is understood that the posts need not to extend entire through the holes for this purpose, though.

As noted above, the spacing between the posts 20 on the base 14 also dictates the spacing between the openings 32 in the cover 22. Desirably, the slots 36 each extend from the same side, and desirably laterally, from the central holes 34. Thus, the spacing between the central holes 34 is approximately equal to the spacing between the slots 36, which is in turn approximately equal to the spacing between the posts 20 on the base.

As also noted above, the leash 24 flexibly connects the platform 21 of the base 14 to the cover 22. Desirably, the leash 24 connects lateral ends of the base 14 and cover 22, so as not to interfere with the mounting of the fitting 11 and catheter along the longitudinal axis. The leash 24 is long enough to permit a desired parallel spacing of the base 14 from the cover 22 when the retainer is in a closed position, as illustrated.

In operation, a catheter (or other medical tube or wire) is inserted into the patient, and the fitting 11 is secured to the catheter. The fitting 11 is then retained within the retainer 10, and the retainer 10 is then secured to the patient. These steps are described in more detail below. While this sequence is advantageous, it will be understood that, in other arrangements, the fitting can be secured to a catheter before or after securing the fitting to the retainer, depending upon the form of the fitting. Similarly, and especially for reapplication of a catheter to the retainer 10, the catheter and fitting 11 can be mounted to the retainer 10 after the retainer 10 has already been secured to the patient.

In the illustrated embodiment, desirably after catheter insertion, the wing clamp 13 is stretched open at the slit 75 and fit over the catheter, as in standard practice. The groove 62 of the box clamp 12 is fitted over the elongate body 70 of the soft wing clamp 13, providing a tight "snap fit." Some flexibility in the wing clamp body 70 facilitates this fitting. The relatively more rigid box clamp body 60, however, exerts relatively more inward pressure on the catheter than the relatively more flexible wing clamp 13, such that a better frictional grip holds the catheter within the fitting 11. It will be understood by one of skill in this art, however, that the fitting 11 of the present embodiment can comprise the soft wing clamp 13 alone.

As shown in FIG. 2, the catheter and fitting 11 are then removably mounted to the retainer 10. In the illustrated embodiment, the holes 77, 67 are fitted over the posts 20 of the retainer base 14. Desirably, each slightly smaller wing clamp hole 77 stretches to accommodate the larger diameter head 26 and ring 28 of the post 20. Each box clamp hole 67, on the other hand, desirably is large enough to receive the head 26 and ring 28 without interference. The fitting 11 is thereby fitted onto the base 14 with the posts 20 extending through the fitting holes 67, 77 and the bottom surface of the soft wing clamp 13 resting on the platform 21.

As illustrated in FIGS. 2 and 3, the cover 22 is latched to the base 14, with the fitting 11 interposed between the cover and the base. FIG. 2 shows the cover 22 in a partially closed position, with the flexible leash 24 bent to position the cover 22 over the base 14. The openings 32 of the cover 22 are aligned with the posts 20 of the base 14 and the cover 22 is then moved toward the base such that the head 26 of each post passes through the central hole 34 of one of the openings 32. The size and spacing of the openings 32 and the posts 22 should result in an easy engagement so that only a light downward force is necessary, thereby avoiding pain or discomfort to the patient. In this position, the portion of the cover 22 between the holes 34 can firmly contact a portion of the fitting 11 in some applications.

The rings 28 can also support, at least in part, the cover 22, or at least limit the travel of the cover 22 over the posts 20 so as to properly position the cover 22 on the posts 22 generally beneath the flared heads 26. Once the heads 26 of the posts 20 have cleared the central holes 34 in the cover 22, the cover 22 contacts the ring 28.

The cover 22 is then slid laterally (to the right, in the views of FIGS. 2 and 3) so that the shaft 25 of each post 20 slides past the narrow waist opening 37 into the corresponding slot 36. The cover material at the waist 37 and/or the shaft 25 slightly compresses as the cover 22 is shifted under force provided by the health care provider. Desirably, the retainer is arranged such that, when the posts 20 are engaged with the slots 36, the cover 22 is centered with respect to the base.

The resulting engagement, shown in FIG. 3, serves to retain the fitting 11 securely in place within the retainer 10. As the waist openings 37 are desirably slightly more narrow than the post shafts 25, the slots 36 provide a friction or snap fit engagement with the posts 20. The slots 36 are longitudinally more narrow than the post heads 26, such that the cover 22 cannot be transversely lifted away from the base 14 in this position. Surfaces of the post 20 abut against surfaces of the cover 22 formed by the lip 38 and walls 46 of the opening 32. The posts 20 of the base 14 and the slotted holes 67, 77 of the cover 22 thereby form a latching structure. The latching structure allows the posts 20 to be easily inserted into the openings 32 in one position but inhibits unintentional retraction of the posts 20 from the openings 32 in a second position.

Additionally, the underside 30 of the post head 26 seats against the cover 22 with the periphery of the head 26 at the edge of the depression 40, as shown. A slight deformation of the head 26 and/or edge of the depression 40 creates increased interference between the cover 22 and the post heads 26 which aids in maintaining the cover 22 in place, relative to the posts 20.

It will be understood that, in other arrangements, the openings can instead be formed in the base, rather than the cover, and the posts formed on the cover. In such a case, each opening would comprise a partial central hole in the base, below which a hollow space is formed for receiving the heads of downward extending posts of the cover. The space would also accommodate the lateral movement of the cover (and consequent lateral movement of the posts) in order to provide engagement between the shaft of each post and a narrow slot extending from the opening. In this manner, the head of one of the posts would be captured within the hollow space below each slot. The post could not be pulled out of the hollow space because the rear side of the post head would contact the portions of the base which define the slot. Such a latching mechanism is disclosed in copending application Ser. No. 08/587,092, entitled "Catheter Anchoring System", filed on Jan. 15, 1996, in the name of Steven F. Bierman and assigned to the assignee hereof, which stands allowed as of the filing date of this application and which is hereby incorporated by reference.

In initial application, the illustrated retainer 10, with the fitting 11 and the catheter retained in it as described above, is secured to the patient by way of the self-adhesive anchor pad 16. The health care provider selects a skin site on which the retainer 10 will be attached. For use with CVCs and PICCs, the retainer 10 desirably is applied to the skin of the patient in the vicinity of the catheter insertion site. The health care provider then cleanses and prepares the anticipated dressing site according to well known methods, usually swabbing with alcohol and allowing the site to dry thoroughly. The health care provider peels away half of the backing layer 17 from the adhesive surface of the anchor pad 16, properly locates the pad 16 on the patient, and presses the exposed adhesive against the patient's skin to secure the anchor pad 16 to the patient. The second half of the backing layer 17 is then removed, and the second half of the anchor pad 17 adhered to the patient's skin. The anchor pad 16 should be mounted on the patient so that catheter overlies the retainer 10 along the retainer's longitudinal axis.

When removal of the catheter becomes necessary, the cover 22 simply is slid horizontally in the opposite direction, desirably with force sufficient to compress cover material at the waists 37, so that the heads 26 of the posts 20 are once again aligned with the central holes 34. The cover 22 can then be easily lifted transversely from the base 14. With the retainer 10 thus unlatched, the fitting 11 can also be removed. The catheter secured by the fitting 11 can then be changed or cleaned and replaced in the retainer 10, without requiring a new retainer.

It should be noted that a deliberate effort is generally required to disengage the post shafts 25 from the slots 36, due to the retention mechanism formed by the narrow neck 37 and/or depression 40. The retainer 10 thus releasably mounts a catheter (or other medical line) and can be reused without requiring reattachment to the patient, while at the same time inhibiting accidental release of the catheter.

Significantly, the removed cover 22 remains leashed to the retainer base 14, which remains attached to the patient. Thus, the health care provider need not take care to place the cover 22 in a safe hygienic place, nor keep track of its whereabouts. The cover 22 can simply hang from the base 14 by the leash 24, where it is easily found and relatched to the base 14 when a new catheter is engaged. Furthermore, each time the cover is relatched, the cover 22 is automatically correctly oriented, such that the health care provider need not take care to ensure that the depression 40 is facing the correct direction, nor to ensure that the slots 36 are on the correct side.

Of course, if the medical treatment is completed and there is no need to reuse the retainer 10, the health care provider can release the cover from the base in the manner described above. The medical article then can be lifted from the base. To remove the anchor pad 16, the health care provider lifts an edge of the pad 16 and gently strokes the undersurface with an alcohol swab while slowly but continuously lifting the edge. The anchor pad 16 can be peeled from the patient's skin in this manner. The health care provider then cleanses and prepares skin using well known hospital or agency protocols.

A retainer 10a in accordance with another embodiment of the invention is illustrated in FIGS. 4A to 5, with FIG. 4A showing a completely open position of the retainer 10a and FIG. 5 showing the partially closed position, similar to FIGS. 1–2 above. Though not illustrated, this retainer 10a also desirably includes a flexible anchor pad, as illustrated in FIG. 1, for adhesive attachment to the body of a patient. Only the cover 22a of this embodiment differs from the above-described embodiment. Accordingly, the above description applies equally to the embodiment of FIGS. 4–5, unless otherwise indicated. In addition, like reference numerals are used to indicate like features of the two embodiments, with the letter "a" added as a suffix to refer to features of the present embodiment.

The cover 22a of this retention mechanism 14a includes a pair of openings 32a. In contrast to the embodiment discussed above, each opening 32a comprises a single slot 80 extending from a longitudinal outer edge 82 of the cover 22a to a terminus 84. The pair of slots 80 can extend from either of the two outer edges 82, but both slots 80 desirably extend from the same edge.

The slots 80 advantageously extend obliquely from the outer edge 82 of the cover 22a to the slot terminus 84, such that one side of each slot 80 defines an obtuse angle a (FIG. 4B) with the outer edge 82 from which the slot extends, as shown in FIG. 4B. The termini 84 of the slots 80 desirably are centered on or close to a lateral line that bisects the cover 22a into longitudinal halves. Thus, the length of each slot 80 depends upon the obtuse angle a between the outer edge 82 and the slot 80. The angle α should be small enough and the slot 80 short enough that the structural integrity of the cover 22a is not compromised. While illustrated as parallel, the slots 80 can also be arranged at a slight angle to one another. The width of each slot 80 desirably is slightly larger than the diameter of the post shaft 25a, and smaller than the largest dimension of the post head 26a.

As best seen from the plan view of FIG. 4B, the opening 32a desirably includes a retention mechanism, such as to inhibit retraction of the post 20a from the slot 80. As visible from the views of FIGS. 4B and 5, each slot 80 is partially defined at the terminus 84 by a lip 38a of cover material, forming a depression 40a in the cover 22a, similar to the lip 38 and depression 40 shown in FIGS. 1–3. The depression 40a is sized slightly smaller than the lower surface 30a of the post head 26a.

In the illustrated embodiment, the retention mechanism further comprises one or more protuberances 86 extending at certain positions from interior walls of the slot 80. As illustrated, the protuberances 86 desirably are positioned within the slot 80 just outside the depression 40a. At the protuberances 86, the slot 36a most desirably has a slightly smaller diameter than the shaft 25a, while widening to slightly larger than the shaft 25a at the lip 38a. These protuberances 86 define the waist 37a of the opening 32a for the present embodiment.

FIG. 5 illustrates the retainer 10a in a partially closed position. The flexible leash 24a has been bent to swing the cover 22a counterclockwise (in the view of FIG. 5), bringing the openings 32a in proximity to the posts 20a. The cover 22a continues in a downward arc from the position of FIG. 5 and is shifted slightly out of alignment with the base 14a until the edge openings of the openings 32a at the longitudinal edge 82 are adjacent to the section of the posts 20a between the head 26a and the ring 28a.

While not illustrated in FIGS. 4A to 5, a catheter fitting can first be mounted to the retainer 10a prior to latching. For example, the fitting 11a illustrated in FIGS. 1–3 can be first secured to the retainer. For such a case, the posts 20a serve as a portion of an interacting structure and the holes 67a, 77a of the fitting 11a serve as another portion of the interacting structure. The interacting structure thus mounts the fitting to the retainer to inhibit at least one degree of movement of the fitting relative to the retainer. Alternatively, a portion of the interacting structure can directly mount a catheter, without the intermediate fitting.

The shaft 25a of each post 20a (between the head 26a and the ring 28a) can be easily inserted into the edge opening of the openings 32a at the outer edge 82. The cover 22a is then shifted obliquely such that the shafts 25a slide along the slots 80. The shafts 25a and/or the protuberances 86 are compressed or the protuberances are deflected as the shafts 25a slide past the protuberances 86. After the shafts 25a have passed the protuberances 86, the shafts and/or the protuberances can regain their original shape such that the shafts snap into the position adjacent to the protuberances 86 and engage with the terminus 84 of the slots 80. When the head 26a is seated at the edge of the depression 40a, the surfaces of the cover 22a formed by the lip 38a and the protuberances 86 of the slot 80 abut against the shaft 25a of the post 20a. The cover 22a is thus latched in a closed position.

In order to remove the cover 22a from the base 14a, the sliding motion of the cover 22a over al the posts 20a is simply reversed until the post shafts 25a exit the openings 32a at the outer edge 82 of the cover 22a. Note that some deliberate force is generally required to overcome the retention mechanism. Namely, the cover 22a is slightly depressed to disengage the underside of the head 26a from the edge of the depression 40a, and the cover 22a is slid with sufficient force to deflect or compress the protuberances 86. Any fitting secured therein can then be disengaged from the opened retainer 10a.

Where the slots are arranged at a slight angle to one another, the friction fit of the posts within the slots will improve, relative to an exactly parallel arrangement. It will be understood that, in other arrangements, a similar slot can extend perpendicularly from the longitudinal edge. Alternatively, slots of each opening can extend from opposite longitudinal edges of the cover. In the latter arrangement, the cover would be aligned longitudinally between the posts and the cover twisted to a lateral alignment, such that the posts each engage the slots on each side. As will be understood by one of skill in this art, such slots would desirably extend along the circumference of a circle centered between the termini.

In either of the above illustrated embodiments, or in inverted arrangements with the posts on the cover, the posts serve both as an interacting structure (for mounting a medical line or fitting) and as a part of the latching structure (for latching the cover to the base). It will be understood, however, from the description of the following two embodiments, that the posts can serve only as part of the latching structure, or only as part of the interacting structure. It will further be understood by one of ordinary skill in this art that the posts can be absent altogether in other arrangements.

FIGS. 6–9 illustrate a retainer 10b in accordance with another embodiment of the present invention. The retainer 10b is shown in an open position in FIG. 6 and in a fully closed and latched position in FIG. 7. Other components of the anchoring system 8b (e.g., anchor pad, catheter adapter) can be the same as described above with respect to FIGS. 1–3. Accordingly, the above description applies equally to the embodiment of FIGS. 6–9, unless otherwise indicated. In addition, like reference numerals are used to indicate like features among the embodiments, with the letter "b" added as a suffix to refer to features of the present embodiment.

The base 14b includes a pair of posts 20b; however, the base can include more or less posts depending upon the application of the anchoring system. Each post 20b has a relatively smooth, continuous surface up to a tip 90 which need not protrude radially from the post 20b, unlike the head 26, 26a of the previously described embodiments. The tip 90 of the post 20b can be a flat surface or can taper into a hemispherical shape (as shown), a conical shape or other well known shapes. In the illustrated embodiment, the posts 20b each consist only of a simple shaft tapered hemispherically at the tip 90. The posts 20b otherwise desirably have the same diameter, spacing, and height of the posts 20, 20a of the previous embodiments. The posts 20b are illustrated as connected to a platform 21b of the base 14a, although it will be appreciated by those skilled in the art, in light of the above disclosure, that the posts could be connected to the cover 22b.

The flexible hinge 24b of this embodiment comprises a relatively rigid support arm 92 that is integrally joined to the platform 21b at a base end 94. As shown in FIG. 6, the support arm 92 extends upwardly from the base end 94 to join with the cover 22b at a thin bridge 96 of cover material. The bridge 96 is formed along a common exterior surface 98 (sec FIG. 7) of the cover 22b and the support arm 92. The bridge 96 is defined along the apex of a notch in the material that forms the cover 22b and support arm 92. The notch 100 can be thought of as the structure formed by a beveled edge sloping away from an interior surface 102 of the cover 22b, conjoined at the bridge 96 with a beveled edge sloping away from an inside surface 104 of the support arm 92.

The hinge 24b flexibly connecting the base 14b to the cover 22b thus comprises the support arm 92, the bridge 96, and the surfaces forming the notch 100. In other arrangements, however, the hinge of an embodiment resembling that of FIGS. 6–9 can comprise a structure similar to a conventional hinge pin-bracket arrangement.

Desirably, the support arm 92, which terminates at an upper end at the bridge 96, has the same height as the posts 20b. It will be understood, however, that the support arm 92 can be higher than the posts 20b in other arrangements.

The thickness of the bridge 96 depends upon the material chosen, and is thick enough to provide the desired strength to connect the support arm 92 to the cover 22b, but thin enough to provide flexibility for opening and closing the retainer 10b. Desirably, the retainer 10b is integrally injection molded of a resilient polymer material, such as polypropylene or polyethylene. For such materials, the bridge 96 has a thickness between about 0.5 mm and 2.5 mm, and desirably about 1.5 mm.

The flexibility of the hinge 24b also depends in part upon the angle formed by surfaces of the notch 100 when the retainer 10b is in the open position shown in FIG. 6. Desirably, the notch 100 defines an angle of at least about 90E, and particularly about 115E. Such an arrangement allows the cover 22b to lie parallel to the platform 21b when the retainer 10b is in the closed position shown in FIG. 7. It will be understood, however, that in other arrangements the closed cover need not lie parallel to the platform 14b (and may take a curvilinear path as described below).

As seen in FIG. 7A, the latching mechanism 110b of the illustrated retainer 10b comprising a fastening pin 112 and a latch having a receptacle 114. The receptacle 114 is configured to receive the fastening pin 112. As shown in FIGS. 6–9, the illustrated fastening pin 112 is integrally connected to the cover 22b and the receptacle 114 is integrally connected to the base 14b. It will be understood, however, that the pin can instead be positioned on the base, while the receptacle is positioned on the cover.

The fastening pin 112 includes a bar 116 extending from the cover 22b (or the base 14b, depending on the position of the element). At the end distal from the connection to the cover 22b, the bar 116 connects to an expanded portion or barb 118 which tapers to a terminus 120 of the pin 112. Like the post head 26, 26a of the previous embodiments, the barb 118 of the fastening pin 112 can be formed in any of a variety of shapes such as an arrowhead (as shown), hemispherical, conical or flexible ribs extending outward from the bar 116. Desirably, the terminus 120 of the fastening pin 112 is relatively blunt and smooth to prevent it from puncturing the gloves of a health care provider or catching on other materials. The barb 118 also desirably includes a sloping or curved surface 121 leading from the terminus 120 to the maximum diameter of the barb 118. At least one shoulder is formed behind the barb 118. In the illustrated embodiment, shoulders are defined on either side of the bar 116.

The receptacle 114 of the latch 110b comprises a pair of opposing tangs 122 that extend to a stem 124 connected to the base 14b (or cover 22b, depending on the position of this element of the latch). Each tang 122 extends outwardly to a lug 126 that can be depressed by finger pressure. Desirably, each tang 122 includes an inner beveled surface 127. These beveled surfaces define an aperture 128 therebetween which tapers from a wider dimension at the top to a narrower dimension at the bottom, where it communicates with a slot 130 located between the opposing stems 124. Each tang defines a downward facing shoulder that cooperates with one of the shoulders of the fastening pin barb 118, as described below.

In operation, a fitting, such as the fitting 11 of FIGS. 1–3, can be first engaged with the posts 20b while the retainer 10b is open (see FIG. 6). Accordingly, the posts 20b of the illustrated embodiment form a portion of the interacting structure for inhibiting movement of a medical line fitting relative to the retainer 10b.

The cover 22b can then swing to a closed position as shown in FIG. 7. The relatively thin strip of material forming the bridge 96 allows the hinge 24b to bend when finger pressure is exerted on the cover 22b to lower it. The angle of the notch 100 further allows the cover 22 to be closed without compressing material between the interior surface 102 of the cover and the inner surface of the support arm 92. While the rigid support arm 92 and the thin bridge 96 permit only rotational and not lateral movement of the cover 22b relative to the base 14b, such lateral movement is not necessary for the illustrated latching mechanism.

The fastening pin 112 can be inserted into the receptacle 114 by positioning the pin 112 into the aperture 128 and pressing on the cover 22b. The sloped surfaces 121 of the fastening pin 112 slide over the beveled inner surfaces 127 of the tangs 122. The interaction of these sloped and beveled surfaces tends to distend the tangs 122 slightly, thereby allowing the barb 118 to enter the slot 130. The tangs 122 then snap back into their original position and engage with the barb 118 of the pin 112 with the corresponding shoulders abutting, thereby releasably securing the cover 22b to the base 14b. FIG. 8 illustrates the closed latch 110b.

When the latch 110b is closed, as shown in FIG. 7, the inner surface 102 of the cover 22b sits atop the tip 90 of the posts 20b, since the posts of the illustrated retainer 10b have the same height as the support arm 92. It will be understood that, in arrangements where the posts are attached to the cover, the tips would abut the base when the cover is in the closed position and latched. Where such contact takes place, a fitting secured between the cover 22b and the base 14b could not slip off the posts 20b when the retainer 10b is closed and latched. Furthermore, the posts 20b provide added support for the cover 22b in the closed position to prevent over-extension of the hinge 24b.

To release the cover 22b from the base 14b, the health care provider can press down on the lugs 126, thereby gaining access to the fitting and/or catheter secured therein. When a lug 126 is depressed, the attached stem 124 bends outward slightly, causing the tang 122 to moved outwardly and the slot 128 to expand, as shown in FIG. 9. To provide friction between the health care provider's finger and the top of the lug 124, ridges or other types of roughened surface can be included.

When only a single lug 124 is depressed, however, the attached tang 122 is elevated until it contacts the surface of the element (e.g., the cover) to which the fastening pin 112 is connected. This degree of elevation of a single tang 122 does not expand the aperture 128 sufficiently to release the barb 118 of the fastening pin 112. In contrast, when both lugs 124 are depressed (not shown), the aperture 128 is sufficiently widened to allow the fastening pin 112 to be readily extracted from the receptacle 114. This design prevents inadvertent release of the fastening pin 112 (e.g., when a lug is bumped), but permits easy opening of the retainer 10b when a health care provider seeks to move the catheter or other fitting held within the retainer 10b.

Figure 11:
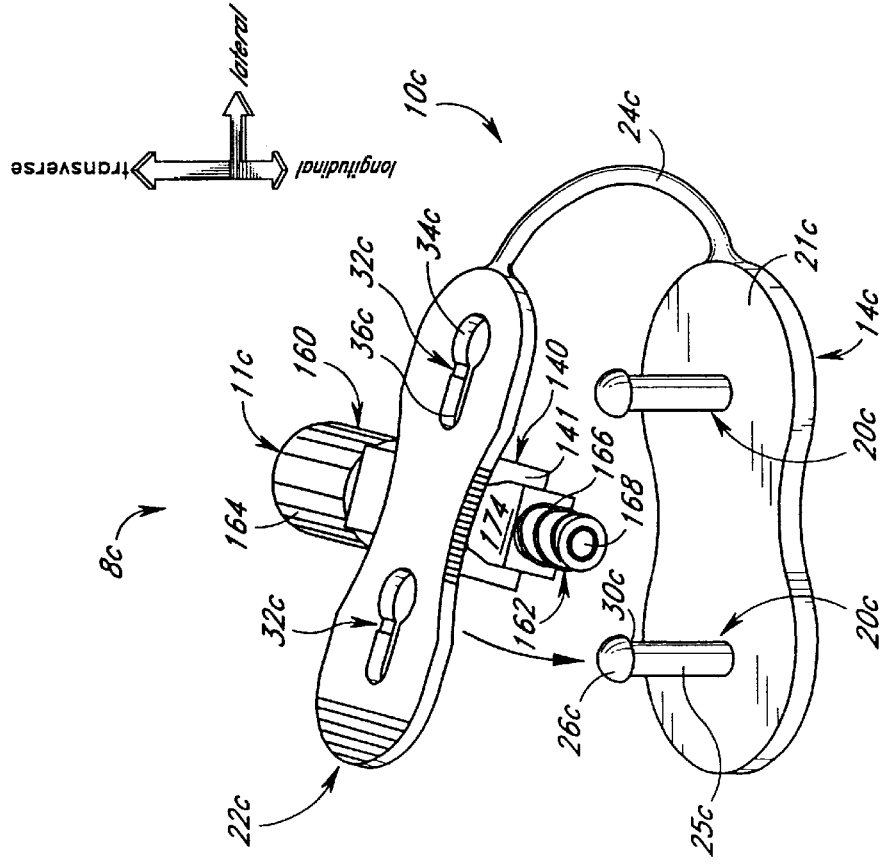
FIG. 11 is a prospective view of the retainer of FIG. 10A, shown in a partially closed position with the cover interacting with the catheter adapter.

FIGS. 10–12 illustrate an anchoring system 8c in accordance with another embodiment of the present invention. Like the anchoring systems described above, the illustrated embodiment includes a retainer 10c, a fitting or adaptor 11c and an anchor pad 16c. The anchor pad 16c desirably is similar to the anchor pad 16 described with respect to FIG. 1. The retainer 10c and the fitting 11c differ somewhat from the above-described embodiments, though certain features are the same. Accordingly, the above description applies equally to the embodiment of FIGS. 10–12, unless otherwise indicated. In addition, like reference numerals are used for like features among the embodiments, with the letter "c" added as a suffix to refer to features of the present embodiment.

The illustrated posts 20c do not include a locator ring of material below the head 26c. The illustrated base 14c, including dimensions of the posts 20c, is otherwise identical to the base 14 described with respect to FIGS. 1–3. Unlike the openings 32, 32a of the previous embodiments, the illustrated opening 32c is shown without a lip or depression in the slot 36c. It will be understood, however, that the slot can also include a depression over which the post head would seat without departing from the principles of the present embodiment.

Like the previous embodiments, the present embodiment includes interengaging structure to mount the medical line to the retainer 10c. In the illustrated embodiment, the interacting structure comprises a channel defined by a mounting structure 140. The channel is sized and shaped to mount a medical line, such as a catheter, either directly or indirectly by way of a fitting. Desirably, the channel defined by the mounting structure 140 is configured to mate with and mount the adaptor 11c which, in turn, engages with the medical line. In the illustrated embodiment, the mounting structure 140 is integrally formed with the cover 22c, such as by injection molding. It will be understood, however, that the mounting structure 140 can equally well be formed as part of the base 14c without materially affecting the function of the retainer 10c.

The illustrated mounting structure 140 comprises two substantially rectangular box-like extensions 141 that extends from the cover 22c between the two openings 32c. The extensions 141 are spaced by a distance sufficient to receive the adaptor 11c and include inner faces 142 configured to mate with surfaces of the adaptor 11c. The inner faces 142 are more particularly shaped to inhibit at least one degree of freedom, desirably to inhibit longitudinal movement of the adaptor 11c when the adaptor is mounted within the channel (see FIG. 11). The illustrated inner faces 142 are convex in shape. The channel defined between the extensions 141, thus, has a minimal width at a central point and widens toward either longitudinal end. In other arrangements, the skilled artisan will recognize that a maximum channel width at a central point will inhibit longitudinal movement of a different fitting. Where, as illustrated, the mounting structure 140 is integral with the cover 22c, the extensions 141 desirably are spaced closely enough to provide a snug or slight interference fit for the adaptor 11c within the channel.

The mounting structure 140 (and the channel defined by it) has a height less than or equal to the height of the post shafts 25c of the base 14c. In the illustrated embodiment, the structure 140 is equal to the height of the shafts 25c, less the thickness of the cover 22c. An outer surface 144 (FIG. 10) of each of the illustrated extensions 141 is accordingly configured to mate with the platform 21c of the base 14c, and is flat in this case.

The cover 22c is illustrated with a slight hourglass shape, such as to provide a slight indentation 146 along an edge 148 of the cover 22c. Desirably, the indentation 146 comprises transverse ridges 150. This shape facilitates an interengagement between the fitting 11c and the mounting structure 140 to inhibit movement of the adaptor 11c at least in the longitudinal direction, as described below.

The fitting 11c of the present embodiment is an in-line adaptor 11c. This adaptor 11c comprises an elongate structure defining a fluid pathway, and means for connecting the adaptor to lines at either end. The illustrated adaptor 11c comprises a medical connector such as those commonly used to connect a supply line to a catheter.

Desirably, the adaptor 11c is of a type similar to that disclosed with respect to FIGS. 11 and 12 of U.S. Pat. No. 5,306,243 ("the '243 patent"), the disclosure of which is hereby incorporated herein by reference. The adaptor 11c includes a male connector 160 for connection to a catheter and a female connector 162 for connection to a medical supply or delivery tube (e.g., leading to an IV drip or a suction pump). The illustrated male connector 160 includes a Luer-type fitting 164 with internal threads and a tapered nose extending outwardly, with an internal passageway for fluid communication with a catheter.

The female connector 162 comprises external threads 166 and a membrane 168 for sealing the internal passageway. The membrane 168 can comprise a closed septum, through which a sharp needle is inserted to provide communication between the supply or delivery tube and the internal passageway. The membrane 168 can also comprise a pre-slit membrane, through which a blunt needle provides communication between the supply or delivery tube and the internal passageway. Desirably, however, the female connector 162 of the adaptor 11c comprises an internal needle integral with the internal passageway, as disclosed in the '243 patent. The membrane 168 comprises a resilient, self-sealing material which is outwardly biased.

An adaptor body 170, between the male connector 160 and the female connector 162, comprises mounting surfaces 172 which form a portion of the interacting structure of the anchoring system 8c. The illustrated mounting surfaces 172 comprise opposed concave surfaces, desirably including ridges (not shown) to facilitate finger gripping during connection of the adaptor 11c to catheters or other medical tubes. In this manner, the adaptor body 170 has a minimal width at a central point and widens toward both the female connector 162 and the male connector 160. In particular, the widest points of the illustrated adaptor 11c are wider than the most narrow portion of the channel between the extensions 141 of the retainer 10c.

The mounting surfaces 172 are joined by a top surface 174 and a bottom surface (not shown). The top and bottom surfaces desirably are flat to mate with the illustrated cover 22c and platform 21c of the retainer 10c, such that these surfaces also form a portion of the interacting structure.

In operation, the adaptor 11c can first be connected to medical tubes. For example, a catheter can be fitted with a female connector with external threading, similar to the female connector 162 of the adaptor 11c. Such a connector can be quickly and easily threaded into the male connector 160 of the adaptor without any external needles, thus reducing the likelihood of needle sticks to the health care provider. While the female connector is threaded into the Luer-type fitting of the male connector 160, the nose of the male connector 160 forces the membrane 168 backwards over the internal needle, thus providing fluid communication between the catheter and the internal passage of the adaptor 11c. Similarly, a medical delivery/supply line can be fitted with a male connector similar to the male connector 160 of the adaptor 11c. Such a connector would then connect with the female connector 162 of the adaptor 11c, thereby completing fluid communication through the adaptor 11c between the delivery/supply line and the catheter.

The adaptor 11c then mounts within the channel defined by the mounting structure 140 of the retainer 10c. In the illustrated embodiment, wherein the mounting structure 140 is formed integrally with the cover 22c, the inner faces 142 of the extensions 141 desirably snugly receive and grip the mounting surfaces 172 of the adaptor 11c.

It will be understood by one of skill in the art, however, that the fit need not be tight enough to inhibit transverse movement of the fitting or adaptor, particularly where the mounting structure is integral to the base, rather than integral to the cover. Desirably, however, the interaction between the mounting structure inner faces 142 and the adaptor mounting surfaces 172 is such as to inhibit significant longitudinal movement (e.g., more than 1–2 mm) of the adaptor 11c. In the illustrated embodiment, the minimal width of the channel is more narrow than the widest portions on either end of the adaptor body 170.

With the adaptor 11c thus mounted to the retainer 10c, the retainer 10c is then be closed and latched, as described with respect to the previous embodiments. Where, as illustrated, the mounting structure 140 is located on the cover 22c, if the mounting structure 140 is not configured for firm engagement, the health care provider can hold the adaptor 11c within the channel until the retainer 10c is latched. FIG. 11 illustrates the retainer 10c in a partially closed condition.

FIG. 12 illustrates the retainer 10c latched closed with the adaptor 11c retained therein. As will be understood by one of skill in the art, the cover 22c and the base 14c interposed the adaptor 11c between them, preventing transverse movement of the adaptor 11c relative to the retainer 14c. The channel defined by the mounting structure 140 inhibits lateral or longitudinal movement of the adaptor 11c relative to the retainer 14c by the cooperating shape of the channel and the adaptor 11c (which form the interengaging structure in this embodiment). Accordingly, the adaptor 11c is sufficiently restrained to secure a catheter extending therefrom to the patient. If the catheter had not been secured to the adaptor prior to engagement of the adaptor to the retainer, the catheter can be secured after engagement.

The skilled artisan will appreciate that the retainers disclosed herein demonstrate versatility in securing a great variety of medical articles to a patient. Retainers similar to those of FIGS. 1–9 can be utilized to secure any device which is provided with holes spaced apart to engage with the posts. The cover is secured to the base to interpose the device between them. Many medical devices are already provided with suture holes which can be fitted over the retainer posts disclosed herein. Other devices can be modified to include such holes. Other arrangements to secure a medical article to the posts, either between the posts or adjacent to a single post, will be readily apparent to those skilled in the art in light of the disclosure herein.

Medical devices can be also be provided with surfaces similar to the mounting surfaces 172 of the illustrated adaptor 11c, for mounting within the integral channel of the retainer 10c illustrated in FIGS. 10–12. Y-joint adapters, for example, can be adapted to mount within the channel of the retainer 10c shown in FIGS. 10–12.

Alternatively, one of skill in the art will readily appreciate that the disclosed retainers can be modified, without departing from the spirit of the invention, to mount and retain existing medical devices. For example, the integral mounting structure illustrated in FIGS. 10–12 can be adapted to clamp existing Y-joint adapters, or to directly mount a catheter or other medical line without the need for an intermediate fitting. In addition, the channel can have a semi-tubular shape and include at least one lateral slot that receives a radially extending member of the adaptor (e.g., an annular collar). Desirably, any such modified mounting structure would inhibit longitudinal and lateral movement of the device or medical line. Transverse movement is inhibited by closure of the retainer with the device or line sandwiched between the base and the cover.

Furthermore, the skilled artisan will recognize the interchangeability of various features from different embodiments. For example, the integral mounting structure 140 of FIGS. 10–12 can be adapted for mounting an adaptor in a retainer having the latch 70 of FIGS. 6–9, thus requiring no posts. Similarly, the various posts, slotted holes, hinges, anchor pads and fittings disclosed herein, as well as other known equivalents for each such feature, can be mixed and matched by one of ordinary skill in this art to construct anchoring systems in accordance with principles of the present invention.

Although not illustrated, each of the illustrated retainers can be adapted for use in an anchoring system which includes a safety loop. An anchor pad larger than the pad 16 illustrated in FIG. 1 can mount both a retainer, in accordance with one of the preferred embodiments, and a separate tube clip. The medical line mounted by the retainer can also be secured less tightly to the tube clip, with an adequate amount of slack in the line between the retainer and the clip. The clip and the resultant slack are desirably located between the retainer and the catheter insertion site, for example.

If movement by the patient causes a sudden pull upon catheter, the catheter slips within the tube clip and the slack length or "safety loop" of the tube is pulled through the clip. Friction between the clip and the sliding tube absorbs some of the force and some of the force causes a slight pull on the adhesive pad, functioning as a warning to the patient to cease the undesirable movement.

Similarly, the retainer itself can be arranged to only slightly inhibit longitudinal movement of a catheter, such as to allow some amount of slip in response to large forces. For example, the fitting of FIGS. 1–3 can comprise a soft wing clamp without the box clamp. In any of these arrangements, a jerk upon the medical line can be largely absorbed by allowing some slip, without either disconnecting the line from the fitting or painfully pulling the anchor pad from the patient's skin.

Using a retainer in accordance with the above disclosure, no painful, invasive or time-consuming sutures or other extensive procedures involving medical sharps (e.g., suture needles) are necessary to anchor an elongate medical article to a patient's skin. In addition, the flexible anchor pad absorbs much of the force incurred in the installation or removal of the retainer and the medical device, thereby providing greater comfort for the patient.

As common to each of the above-described retainers and anchoring systems, the present invention provides a sterile, tight-gripping, needle-free way to anchor medical articles to a patient. The retainers thus eliminate accidental needle sticks, suture wound site infections and scanning because sutures are not required. In addition, the retainers can be used with any of a wide variety of catheters, tubes, wires, and other medical articles to provide universal securement using one style of retainer. Also, patient comfort is enhanced and application time is decreased with the use of the present retainer.

The releasable engagement of the cover and the base allow the same retainer to be used more than once on the same patient at the application location. That is, a first medical device can be mounted in the retainer. When the function of the first medical device is accomplished, the retainer can be unlatched, the first device removed, and a second medical device can be retained in the same retainer. Furthermore, the leash or hinge connecting the cover to the base ensures that the cover will not be lost or misplaced during a catheter change. The health care provider wastes no time in searching for a cover, nor in orienting the cover prior to latching.

Although this invention has been described in terms of certain preferred embodiments and suggested possible modifications thereto, other embodiments and modifications apparent to those of ordinary skill in the art are also within the scope of this invention. Accordingly, the scope of the invention is intended to be defined only by the claims which follow.

What is claimed is:

1. A method of securing a medical device to the body of a patient, the method comprising the steps of:

providing a retainer including a base that defines a receiving area for receiving a portion of the medical device, a cover permanently coupled to the base, the cover being movable between a closed position, in which at least a portion of the cover extends over at least a portion of the receiving area, and an open position, in which the receiving area is at least partially open, a latching mechanism operating between the base and the cover to releasably latch the cover to the base with the cover in the closed position, and interacting structure which is adapted to engage the medical device in a non-occlusive manner and to limit longitudinal movement of the medical device through the retainer when the medical device is placed within the receiving area;

positioning the retainer on the body of the patient;

attaching the retainer to the body of the patient with an adhesive layer;

securing a portion of the medical device in the receiving area of the base;

moving the cover over the base so that the cover is located over at least a portion of the interacting structure; and securing the cover in position upon the base using the latching mechanism.

2. The method of claim 1 wherein the step of providing a retainer further comprises providing a retainer having a channel which lies between the base and the cover of the retainer when the cover is in the closed position.

3. The method of claim 2 wherein the step of providing a retainer further comprises providing a retainer having the interacting structure of the retainer comprise a post which extends at least partially into the channel of the retainer.

4. The method of claim 3 wherein the step of securing a portion of the medical device comprises inserting the post of the retainer through a hole in the medical device.

5. The method of claim 2 wherein the step of providing a retainer further comprises providing a retainer having a channel that has a variable cross section along its length.

6. The method of claim 2 wherein the step of securing a portion of the medical device comprises placing a portion of the medical device within the channel of the retainer.

7. The method of claim 2 wherein the step of providing a retainer further comprises providing a retainer in which the cross section of the channel tapers along its length.

8. The method of claim 1 wherein the step of providing a retainer further comprises providing a retainer having the cover of the retainer coupled to the base of the retainer by a flexible hinge.

9. The method of claim 8 wherein the step of providing a retainer further comprises providing a retainer having the flexible hinge comprise an elongate leash extending between the cover and the base.

10. The method of claim 8 wherein the step of providing a retainer further comprises providing a retainer having a flexible hinge comprise a rigid support arm fixed to the base and a flexible bridge extending between the support arm and the cover.

11. The method of claim 8 wherein the step of providing a retainer further comprises providing a retainer in which the base, cover and hinge are integrally formed.

12. A method of securing a medical line to the body of a patient, the method comprising the steps of:

providing a retainer attachable to a medical line, including a base, a cover permanently coupled to the base, a latching mechanism, a channel, and an adhesive layer attached to the retainer, the cover being movable between an open position and a closed position, the latching mechanism releasably latching the cover to the base in the closed position, the channel being disposed between the base and the cover when the cover is in the closed position, the channel being shaped to retain the medical line between the cover and the base with the cover in the closed position in order to inhibit movement of the medical line in a direction generally parallel to the medical line's longitudinal axis;

positioning the retainer on the body of the patient;

attaching the adhesive layer to the body of the patient;

placing a portion of the medical line into the channel;

moving the cover over the base so that the medical line is retained within the channel; and securing the cover in position upon the base using the latching mechanism.

13. The method of claim 12 wherein the step of providing a retainer further comprises providing a retainer having a post which extends at least partially into the channel of the retainer.

14. The method of claim 13 wherein the step of securing a portion of the medical device comprises inserting the post of the retainer through a hole in the medical device.

15. the method of claim 12 wherein the step the step of providing a retainer further comprises providing a retainer in which the channel has a variable cross section along its length.

16. The method of claim 12 wherein the step of securing a portion of the medical device comprises placing a portion of the medical device within the channel of the retainer.

17. The method of claim 12 wherein the step of providing a retainer further comprises providing a retainer in which the cross section of the channel tapers along its length.

18. The method of claim 12 wherein the step of providing a retainer further comprises providing a retainer in which the cover of the retainer is coupled to the base of the retainer by a flexible hinge.

19. The method of claim 18 wherein the step of providing a retainer further comprises providing a retainer in which the flexible hinge comprises an elongate leash extending between the cover and the base.

20. The method of claim 18 wherein the step of providing a retainer further comprises providing a retainer having a flexible hinge that comprises a rigid support arm fixed to the base and a flexible bridge extending between the support arm and the cover.

21. The method of claim 18 wherein the step of providing a retainer further comprises providing a retainer in which the base, cover and hinge are integrally formed.

22. A method of securing a medical line to the body of a patient, the method comprising the steps of:

providing a retainer, the retainer including a base that defines a receiving area for receiving a portion of the medical line and a cover coupled to the base, means for releasably latching the cover to the base, and means for limiting longitudinal movement of the medical line relative to the retainer;

positioning the retainer on the body of the patient;

attaching the adhesive layer to the body of the patient;

placing a portion of the medical line into the receiving area;

moving the cover over the base so that the cover lies at least partially over the movement limiting means; and securing the cover in position upon the base using the latching mechanism.

* * * * *

(12) INTER PARTES REEXAMINATION CERTIFICATE (606th)
United States Patent
Bierman

(10) Number: US 6,447,485 C1
(45) Certificate Issued: May 30, 2013

(54) MEDICAL LINE ANCHORING SYSTEM

(75) Inventor: Steven F. Bierman, Del Mar, CA (US)

(73) Assignee: Venetec International, Inc., San Diego, CA (US)

Reexamination Request:
No. 95/000,271, Jun. 25, 2007

Reexamination Certificate for:
Patent No.: 6,447,485
Issued: Sep. 10, 2002
Appl. No.: 09/797,341
Filed: Mar. 1, 2001

Related U.S. Application Data

(62) Division of application No. 08/865,231, filed on May 29, 1997, now Pat. No. 6,213,979.

(51) Int. Cl.
*A61M 5/32* (2006.01)
(52) U.S. Cl.
USPC ..... 604/174; 604/180; 604/177; 128/DIG. 26
(58) Field of Classification Search
None
See application file for complete search history.

(56) References Cited

To view the complete listing of prior art documents cited during the proceeding for Reexamination Control Number 95/000,271, please refer to the USPTO's public Patent Application Information Retrieval (PAIR) system under the Display References tab.

*Primary Examiner* — Beverly M. Flanagan

(57) ABSTRACT

An anchoring system includes a simply-structured device which permits a portion of a catheter tube or similar medical article to be easily anchored to a patient, desirably without the use of tape or needles and suturing. A unitary retainer desirably includes a base connected to a cover by way of a flexible hinge. The retainer is attached to a flexible anchor pad including an adhesive bottom surface, which can be attached to the patient's skin. A catheter is secured to a fitting, which in turn mounts to the retainer. Mounting the fitting to the retainer can be accomplished by inserting posts of the retainer through holes of the fitting, or by mounting the fitting within a channel defined by mounting structures integral to the retainer. The cover is then positioned over the base, by bending the flexible hinge, and latched to the base. Several embodiments of the latching mechanism are disclosed. In one form, the latching mechanism includes one or more posts on the base which can be releasably locked into corresponding slotted holes in the cover.

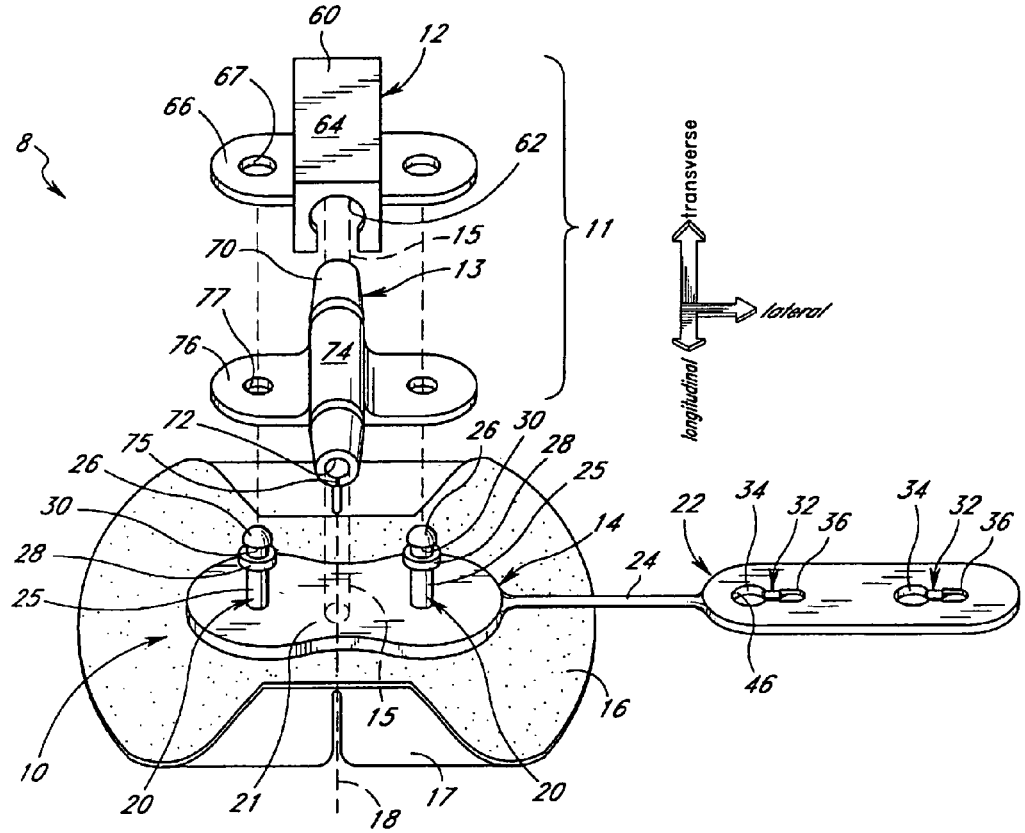

US 6,447,485 C1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3, 5-8, 11, 12 and 22 are cancelled.

Claims 13 and 15-18 are determined to be patentable as amended.

Claim 21, dependent on an amended claim, is determined to be patentable.

New claims 23-26 are added and determined to be patentable.

Claims 4, 9, 10, 14, 19 and 20 were not reexamined.

13. [The method of claim 12 wherein the step of providing a retainer further comprises providing a retainer having] *A method of securing a medical line to the body of a patient, the medical line having an irregularly shaped portion, the method comprising the steps of:*
   *providing a retainer attachable to a medical line, including a base, a cover permanently coupled to the base, a latching mechanism, a channel,* a post which extends at least partially into the channel of the retainer, *and an adhesive layer attached to the retainer, the cover being movable between an open position and a closed position, the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the irregularly shaped portion of the medical line in a direction generally parallel to the medical line's longitudinal axis;*
   *positioning the retainer on the body of the patient;*
   *attaching the adhesive layer to the body of the patient;*
   *placing a portion of the medical line into the channel;*
   *moving the cover over the base so that the medical line is retained within the channel; and*
   *securing the cover in position upon the base using the latching mechanism.*

15. [the method of claim 12 wherein the step the step of providing a retainer further comprises providing a retainer in which the channel has] *A method of securing a medical line to the body of a patient, the medical line having an irregularly shaped portion, the method comprising the steps of:*
   *providing a retainer attachable to a medical line, including a base, a cover permanently coupled to the base, a latching mechanism, a channel having* a variable cross section along its length, *and an adhesive layer attached to the retainer, the cover being movable between an open position and a closed position, the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the irregularly shaped portion of the medical line in a direction generally parallel to the medical line's longitudinal axis;*
   *positioning the retainer on the body of the patient;*
   *attaching the adhesive layer to the body of the patient;*
   *placing a portion of the medical line into the channel;*
   *moving the cover over the base so that the medical line is retained within the channel; and*
   *securing the cover in position upon the base using the latching mechanism.*

16. [The method of claim 12 wherein the step of securing a portion of the medical device comprises] *A method of securing a medical line to the body of a patient, the medical line having an irregularly shaped portion, the method comprising the steps of:*
   *providing a retainer attachable to a medical line, including a base, a cover permanently coupled to the base, a latching mechanism, a channel, and an adhesive layer attached to the retainer, the cover being movable between an open position and a closed position, the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the irregularly shaped portion of the medical line in a direction generally parallel to the medical line's longitudinal axis;*
   *positioning the retainer on the body of the patient;*
   *attaching the adhesive layer to the body of the patient;*
   placing a portion of the medical device within the channel of the retainer;
   *moving the cover over the base so that the medical line is retained within the channel; and*
   *securing the cover in position upon the base using the latching mechanism.*

17. [The method of claim 12 wherein the step of providing a retainer further comprises providing a retainer in which] *A method of securing a medical line to the body of a patient, the medical line having an irregularly shaped portion, the method comprising the steps of:*
   *providing a retainer attachable to a medical line, including a base, a cover permanently coupled to the base, a latching mechanism, a channel wherein* the cross section of the channel tapers along its length, *and an adhesive layer attached to the retainer, the cover being movable between an open position and a closed position, the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the* irregularly shaped portion of the medical line in a direction generally parallel to the medical line's longitudinal axis;
positioning the retainer on the body of the patient;
attaching the adhesive layer to the body of the patient;
placing a portion of the medical line into the channel;
moving the cover over the base so that the medical line is retained within the channel; and
securing the cover in position upon the base using the latching mechanism.

18. [The method of claim 12 wherein the step of providing a retainer further comprises providing a retainer in which] *A method of securing a medical line to the body of a patient, the medical line having an irregularly shaped portion, the method comprising the steps of:*
*providing a retainer attachable to a medical line, including a base, a cover permanently coupled to the base, a latching mechanism, a channel, and an adhesive layer attached to the retainer, the cover being moveable between an open position and a closed position wherein* the cover of the retainer is coupled to the base of the retainer by a flexible hinge, *the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the irregularly shaped portion of the medical line in a direction generally parallel to the medical line's longitudinal axis;*
*positioning the retainer on the body of the patient;*
*attaching the adhesive layer to the body of the patient;*
*placing a portion of the medical line into the channel;*
*moving the cover over the base so that the medical line is retained within the channel; and*
*securing the cover in position upon the base using the latching mechanism.*

*23. A method of securing a medical line to the body of a patient, the medical line having an irregularly shaped portion, the method comprising the steps of:*
*providing a retainer attachable to a medical line, including a base, a cover permanently coupled to the base, a latching mechanism, a channel, and an adhesive layer attached to the retainer, the cover being movable between an open position and a closed position, the latching mechanism releasably latching the cover to the base in the closed position, the channel being disposed between the base and the cover when the cover is in the closed position, the channel having an irregular shape along its length that substantially corresponds in shape to the irregularly shaped portion of the medical line to retain the irregularly shaped portion of the medical line between the cover and the base with the cover in the closed position in order to inhibit movement of the irregularly shaped portion of the medical line in a direction generally parallel to the medical line's longitudinal axis;*
*positioning the retainer on the body of the patient;*
*attaching the adhesive layer to the body of the patient;*
*placing a portion of the medical line into the channel, wherein the portion is a catheter fitting;*
*moving the cover over the base so that the medical line is retained within the channel; and*
*securing the cover in position upon the base using the latching mechanism.*

*24. The method of claim 13, wherein the step of securing the cover in position upon the base further comprises disposing at least part of the post above the cover.*

*25. The method of claim 22, wherein the portion of the medical line placed within the receiving area is a catheter fitting, and wherein the means for limiting longitudinal movement is adapted to engage between the catheter fitting.*

*26. The method of claim 25, wherein the means for limiting longitudinal movement is adapted to engage a fitting at multiple locations.*

\* \* \* \* \*